(12) United States Patent
Altmann et al.

(10) Patent No.: US 7,918,793 B2
(45) Date of Patent: Apr. 5, 2011

(54) SYNCHRONIZATION OF ULTRASOUND IMAGING DATA WITH ELECTRICAL MAPPING

(75) Inventors: Andres Claudio Altmann, Haifa (IL); Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 271 days.

(21) Appl. No.: 11/262,217

(22) Filed: Oct. 28, 2005

(65) Prior Publication Data

US 2007/0106146 A1 May 10, 2007

(51) Int. Cl.
*A61B 8/00* (2006.01)
*A61B 5/05* (2006.01)
*G06K 9/00* (2006.01)

(52) U.S. Cl. ........ 600/437; 600/407; 600/424; 600/450; 600/466; 382/128

(58) Field of Classification Search .................. 600/437, 600/450, 407, 466, 428, 424; 345/629; 382/128
See application file for complete search history.

(56) References Cited

U.S. PATENT DOCUMENTS

| | | | |
|---|---|---|---|
| 5,738,096 A | 4/1998 | Ben-Haim | |
| 5,873,822 A * | 2/1999 | Ferre et al. | 600/407 |
| 6,226,542 B1 * | 5/2001 | Reisfeld | 600/407 |
| 6,332,089 B1 | 12/2001 | Acker et al. | |
| 6,618,612 B1 | 9/2003 | Acker et al. | |
| 6,650,927 B1 | 11/2003 | Keidar | |
| 6,690,963 B2 | 2/2004 | Ben-Haim et al. | |
| 6,716,166 B2 | 4/2004 | Govari | |
| 6,773,402 B2 | 8/2004 | Govari et al. | |
| 2002/0065455 A1 | 5/2002 | Ben-Haim et al. | |
| 2003/0013958 A1 * | 1/2003 | Govari et al. | 600/437 |
| 2003/0128801 A1 | 7/2003 | Eisenberg et al. | |
| 2004/0068178 A1 | 4/2004 | Govari | |
| 2004/0077952 A1 | 4/2004 | Rafter et al. | |
| 2004/0147920 A1 | 7/2004 | Keidar | |
| 2005/0050098 A1 * | 3/2005 | Barnett | 707/104.1 |
| 2005/0080336 A1 * | 4/2005 | Byrd et al. | 600/428 |
| 2005/0207526 A1 | 9/2005 | Altman | |

FOREIGN PATENT DOCUMENTS

| | | |
|---|---|---|
| EP | 0974936 B1 | 1/2000 |
| EP | 1350470 B1 | 5/2005 |
| WO | WO 01/20552 A1 | 3/2001 |
| WO | 03/046599 A1 | 6/2003 |

(Continued)

OTHER PUBLICATIONS

Gepstein L., et al., A Novel Method for Nonfluoroscopic Catheter-Based Electroanatomical Mapping of the Heart, Circulation, 1997; 95:1611-1622, pp. 1-34.*

(Continued)

*Primary Examiner* — Long V Le
*Assistant Examiner* — Katherine L Fernandez
(74) *Attorney, Agent, or Firm* — Louis J. Capezzuto

(57) ABSTRACT

An image of an electro-anatomical map of a body structure having cyclical motion is overlaid on a 3D ultrasonic image of the structure. The electro-anatomical data and anatomic image data are synchronized by gating both electro-anatomical data acquisition and an anatomic image at a specific point in the motion cycle. Transfer of image data includes identification of a point in the motion cycle at which the 3-dimensional image was captured or is to be displayed.

31 Claims, 14 Drawing Sheets

FOREIGN PATENT DOCUMENTS

WO    WO 2004/049928 A1    6/2004

OTHER PUBLICATIONS

Simon R.D.B. et al.: "Electronanatomic Mapping of the Right Atrium with a Right Atrial Basket Catheter and Three-Dimensional Intracardiac Echocardiography"; PACE- Pacing and Clinical Electrophysiology; Mar. 2004, pp. 318-326; vol. 27, No. 3, Blackwell Futura Publishing, Malden, MA, US.

European Search Report No. EP 06 25 5546 dated Sep. 27, 2009.

EP Search Report No. Ep 10 07 5188 Dated Jun. 4, 2010.

* cited by examiner

SYNCHRONIZATION OF ULTRASOUND IMAGING DATA WITH ELECTRICAL MAPPING

BACKGROUND OF THE INVENTION

1. Field of the Invention

This invention relates to anatomic cardiac imaging and electro-anatomical mapping. More particularly, this invention relates to synchronized display of 3-dimensional ultrasound images and electro-anatomical maps of the heart.

1. Description of the Related Art

The meanings of acronyms and certain terminology used herein are given in Table 1.

TABLE 1

| | |
|---|---|
| CT | Computed Tomography; Computed Tomographic |
| ECG | Electrocardiogram |
| HIFU | High Intensity Focused Ultrasound |
| IOD | Information Object Definition |
| MRI | Magnetic Resonance Imaging |
| PET | Positron Emission Tomography |

Methods for three-dimensional geometrical mapping and reconstruction of the endocardial surface are known in the art. For example, U.S. Pat. No. 5,738,096, whose disclosure is incorporated herein by reference, describes methods for mapping the endocardium based on bringing a probe into contact with multiple locations on a wall of the heart, and determining position coordinates of the probe at each of the locations. The position coordinates are combined to form a map of at least a portion of the heart. These methods are effective and accurate, but they require substantial time and skill to carry out.

Hybrid catheters are now known that perform ultrasound imaging in conjunction with position sensing. Such devices are disclosed, for example, in commonly assigned U.S. Pat. Nos. 6,690,963, 6,716,166 and 6,773,402, which are herein incorporated by reference. Medical applications include 3-dimensional mapping of a cavity of the body, as well as measurement of chamber wall thickness and wall velocity and mapping of electrical activity. In medical applications, it is common to acquire maps and images of body organs by different modalities, which are to be interpreted in relationship to one another. An example is correlation of an electro-anatomical map of the heart and an image, such as a 3-dimensional ultrasound image.

Commercial electrophysiological and physical mapping systems based on detecting the position of a probe inside the body are presently available. Among them, the Carto-Biosense® Navigation System, available from Biosense Webster Inc., 3333 Diamond Canyon Road Diamond Bar, Calif. 91765, is a system for automatic association and mapping of local electrical activity with catheter location.

SUMMARY OF THE INVENTION

Both ultrasound imaging and electro-anatomical maps are methods that may be used to diagnose and monitor conditions of the heart, such as ischemia and infarction. When used together, the two monitoring techniques can provide greater diagnostic accuracy than either technique alone. In addition, the two methods can be used in conjunction with ablation to confirm that an intended region has been ablated.

One difficulty that may arise in registering the electro-anatomical map and the 2-dimensional and 3-dimensional ultrasound images is that the shape of the heart chambers changes during the cardiac cycle. Thus, there may be a discrepancy between the locations of points on the heart wall at which electrical measurements are made and the locations at which these points appear in the ultrasound image. This discrepancy may cause distortion in the presentation of the electro-anatomical map and confusion in the doctor's interpretation of the information.

Previous approaches have involved ECG gating in electro-anatomical mapping systems, in which electro-anatomical maps are typically superimposed on pre-acquired 3-dimensional images. Such systems are unable to display 3-dimensional anatomic images concurrently with electro-anatomical maps in realtime.

When 2-dimensional images of a moving organ, such as the heart, are captured, the images are generally built up over time in synchronization with the movement of the organ. CT images of the heart, for example, are captured in synchronization with a body surface ECG signal, so that all the CT slices are generated at the same point in the heart cycle. In the absence of such synchronization, the 3-dimensional image would be hopelessly blurred. Different 3-dimensional images may be formed at different points in the heart cycle. Additionally or alternatively, images of the heart and other organs in the thorax may be synchronized with the respiratory cycle.

When an electro-anatomical map or other near realtime map or image is to be registered with a preacquired 2-dimensional or 3-dimensional image of the heart or other moving organ, it is important to know the point in the motion cycle at which the image was acquired, in order to achieve proper registration between the map and image. The present invention provides a protocol for transferring synchronization information from an imaging device to an electro-anatomical mapping device. In an embodiment employing the Carto-Biosense Navigation System, when an imager, such as a CT, MRI, PET or ultrasound scanner, transfers an image to the Carto-Biosense Navigation System, it also transfers synchronization data corresponding to the image, such as an identification of the point in an ECG or respiratory cycle at which the image was captured.

According to a disclosed embodiment of the invention, near realtime anatomical information, such as ultrasound information, is analyzed and displayed in conjunction with an electro-anatomical map. As used herein, the term "near realtime" refers the interval required to acquire and process data or images during an operative session, e.g., an interval that begins at the acquisition of anatomic data as a series of 2-dimensional images, and terminates following its reconstruction into a 3-dimensional image, all of which occur during an imaging session with a subject or immediately thereafter. In one embodiment, the present invention provides apparatus and methods for generating and presenting in near realtime an electro-anatomical map of a heart chamber overlaid on a 3-dimensional ultrasonic image of the chamber. The 3-dimensional ultrasonic image is reconstructed by combining multiple 2-dimensional images in different positions and orientations. The electro-anatomical information may be superimposed on the 3-dimensional image by coloring the image. The electro-anatomical data and anatomic imaging data are synchronized by gating both electro-anatomical data acquisition and an anatomic image at a specific point in the cardiac cycle. A constant defined offset between the electro-anatomical data and anatomic imaging gating compensates for the ultrasound system image processing and image transfer between two acquisition systems. The gating point is typically determined by triggering both electrocardiographic and anatomic imaging systems on the ECG signal as measured by a body surface electrode or intracardiac ECG signals. Common gating of electro-anatomical and anatomic image acquisition is useful in generating combined 3-dimensional image maps with high anatomical accuracy. Embodiments of the invention can be applied to other body structures having cyclical motion, for example respiratory structures.

In contrast with conventional anatomic images, e.g., ultrasound images, which are most frequently gated at either systole or diastole, in embodiments of the present invention gating is performed at any point in an imaged structure's motion cycle. This feature permits an operator to choose the most appropriate phase or phases at which to create image maps. The ability to select a gating point is particularly important in cardiac applications, when ablation is to be performed, particularly when the heart is in a state of fibrillation. In such case the points of systole and diastole are difficult or impossible to define accurately.

Although the embodiments described herein relate mainly to the combination of ultrasound images with electro-anatomical maps, the principles of the present invention may similarly be applied in synchronized superimposition of functional-anatomical map information (both electrical and other types) on images made using other modalities, as well, such as CT and MRI.

The invention provides a method for displaying images of a cyclically moving structure in a body of a living subject, which is carried out by selecting a gating point in a motion cycle of the structure, acquiring data of the structure using an imaging device, acquiring position data that includes the location and orientation of the imaging device, outputting the data of the structure and the position data, and synchronizing the output of the data of the structure with the output of the position data relative to the gating point.

An aspect of the method includes transferring the synchronized data of the structure and the synchronized position data to a processing device.

Yet another aspect of the method includes displaying the synchronized data of the structure in registration with the synchronized position data.

A further aspect of the method includes constructing an image of the structure from at least one of the data of the structure and the position data.

According to another aspect of the method, the imaging device is an ultrasound transducer.

According to one aspect of the method, the data of the structure is an electro-anatomical map.

According to additional aspects of the method, the data of the structure can be one-dimensional data, two-dimensional data, or three-dimensional data.

In a further aspect of the method the data of the structure includes a plurality of frames acquired at different phases of the motion cycle, which are synchronized by associating the frames with a corresponding portion of the output of the position data.

In another aspect of the method, synchronizing comprises generating an energy pulse while acquiring the data of the structure, associating one of the frames with the energy pulse, and determining a time offset between the one frame and the corresponding portion of the output of the position data.

In one aspect of the method, data of the structure and position data are acquired concurrently.

In an additional aspect of the method data of the structure and position data are acquired non-concurrently.

The invention provides a method for displaying images of a cyclically moving structure in a body of a living subject, which is carried out by selecting a gating point in a motion cycle of the structure, acquiring first data of the structure using a first modality, acquiring second data of the structure using a second modality, outputting the first data and the second data, and synchronizing the output of the first data with the output of the second data relative to the gating point.

The invention provides a system for displaying images of a cyclically moving structure in a body of a living subject, including electrical circuitry operative for selecting a gating point in a motion cycle of the structure, a first acquisition device operative for acquiring first data of the structure using a first modality, a second acquisition device operative for acquiring second data of the structure using a second modality, a processor operative for synchronizing an output of the first acquisition device with an output of the second acquisition device relative to the gating point and for generating a first visual display from the output of the first acquisition device and a second visual display from the output of the second acquisition device. The system includes a display device linked to the processor for displaying the first visual display in registration with the second visual display.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

System Overview

Figure 1:
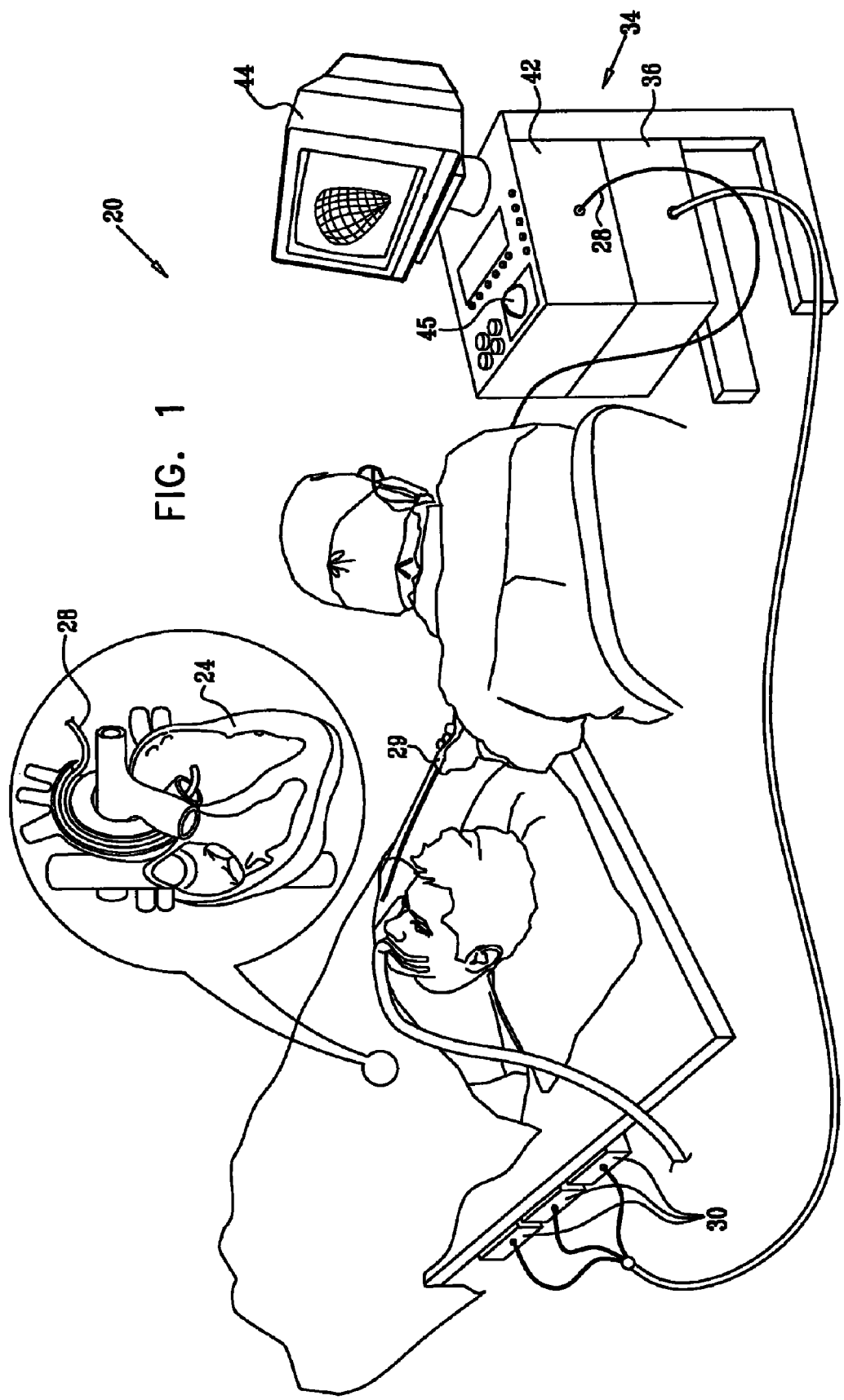
FIG. 1 is a schematic, pictorial illustration of a system for acquiring anatomic images and electro-anatomical maps of the heart, in accordance with a disclosed embodiment of the invention.

Turning now to the drawings, reference is initially made to FIG. 1, which is an illustration of a system 20 for imaging and mapping a heart 24 of a patient, in accordance with an embodiment of the present invention. The system comprises a catheter 28, which is inserted by a physician into a chamber of the heart through a vein or artery. The catheter 28 typically comprises a handle 29 for operation of the catheter by the physician. Suitable controls on the handle enable the physician to steer, position and orient the distal end of the catheter as desired.

The system 20 comprises a positioning subsystem that measures location and orientation coordinates of the catheter 28. (Throughout this patent application, the term "location" refers to the spatial coordinates of the catheter, and the term "orientation" refers to its angular coordinates. The term "position" refers to the full positional information of the catheter, comprising both location and orientation coordinates.)

In one embodiment, the positioning subsystem comprises a magnetic position tracking system that determines the position and orientation of the catheter 28. The positioning subsystem generates magnetic fields in a predefined working volume its vicinity and senses these fields at the catheter. The positioning subsystem typically comprises a set of external radiators, such as field generating coils 30, which are located in fixed, known positions external to the patient. The coils 30 generate fields, typically electromagnetic fields, in the vicinity of the heart 24. The generated fields are sensed by a position sensor 32 inside the catheter 28.

In an alternate embodiment, a radiator in the catheter, such as a coil, generates electromagnetic fields, which are received by sensors outside the patient's body.

The position sensor transmits, in response to the sensed fields, position-related electrical signals over cables 33 running through the catheter to a console 34. Alternatively, the position sensor may transmit signals to the console over a wireless link. The console comprises a positioning processor 36 that calculates the location and orientation of the catheter 28 based on the signals sent by position sensor 32. The positioning processor 36 typically receives, amplifies, filters, digitizes, and otherwise processes signals from the catheter 28.

Some position tracking systems that may be used for this purpose are described, for example, in U.S. Pat. Nos. 6,690,963, 6,618,612 and 6,332,089, and U.S. Patent Application Publications 2002/0065455 A1, 2004/0147920 A1 and 2004/0068178 A1, whose disclosures are all incorporated herein by reference. Although the positioning subsystem shown in FIG. 1 uses magnetic fields, the methods described below may be implemented using any other suitable positioning subsystem, such as systems based on electromagnetic fields, acoustic or ultrasonic measurements.

Alternatively, the system 20 can be realized as the above-referenced Carto-Biosense Navigation System, suitably modified to execute the procedures described hereinbelow. For example, the system 20 may be adapted, mutatis mutandis, to employ the catheters disclosed in the above-noted U.S. Pat. Nos. 6,716,166 and 6,773,402 in order to pre-acquire electro-anatomical data for an electro-anatomical map, and then display near realtime ultrasound images concurrently with an image of the pre-acquired electro-anatomical map in the same or different sessions, and in many different combinations.

As will be explained and demonstrated below, the system 20 enables the physician to perform a variety of mapping and imaging procedures. These procedures comprise, for example, the following in different combinations:

displaying real-time or near realtime 2-dimensional ultrasound images (gated images);

reconstructing 3-dimensional models of a target structure in the patient's body, based on 2-dimensional ultrasound images;

optionally overlaying and displaying a parametric map, such as an electro-physiological information map or an electro-anatomical map on the reconstructed 3-dimensional model;

registering, overlaying and displaying a 3-dimensional image acquired from an external system on the reconstructed 3-dimensional model; and displaying 2-dimensional ultrasound images on a 3-dimensional image acquired from an external system.

Figure 2:
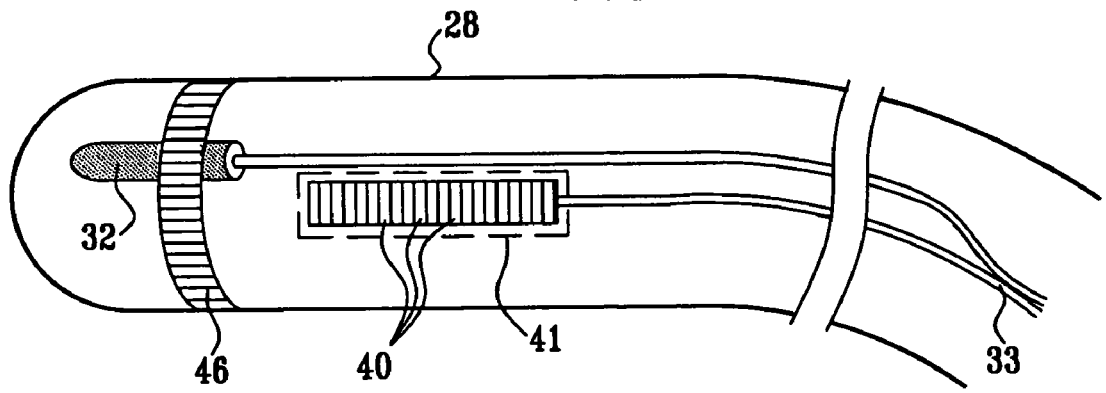
FIG. 2 schematically illustrates the distal end of a catheter used in the system shown in FIG. 1, in accordance with an embodiment of the present invention.

Reference is now made to FIG. 2, which schematically illustrates an embodiment of the distal end of the catheter 28 (FIG. 1), in accordance with an embodiment of the present invention. The catheter 28 comprises an ultrasonic imaging sensor. The ultrasonic sensor typically comprises an array of ultrasonic transducers 40. In one embodiment, the transducers are piezo-electric transducers. The ultrasonic transducers are positioned in or adjacent to a window 41, which defines an opening within the body or wall of the catheter.

The transducers 40 operate as a phased array, jointly transmitting an ultrasound beam from the array aperture through the window 23. Although the transducers are shown arranged in a linear array configuration, other array configurations can be used, such as circular or convex configurations. In one embodiment, the array transmits a short burst of ultrasound energy and then switches to a receiving mode for receiving the ultrasound signals reflected from the surrounding tissue. Typically, the transducers 40 are driven individually in a controlled manner in order to steer the ultrasound beam in a desired direction. By appropriate timing of the transducers, the produced ultrasound beam can be given a concentrically curved wave front, so as to focus the beam at a given distance from the transducer array. Thus, the system 20 (FIG. 1) uses the transducer array as a phased array and implements a transmit/receive scanning mechanism that enables the steering and focusing of the ultrasound beam, so as to produce 2-dimensional ultrasound images.

In one embodiment, the ultrasonic sensor comprises between sixteen and sixty-four transducers 40, preferably between forty-eight and sixty-four transducers. Typically, the transducers generate the ultrasound energy at a center frequency in the range of 5-10 MHz, with a typical penetration depth of 14 cm. The penetration depth typically ranges from several millimeters to around 16 centimeters, and depends upon the ultrasonic sensor characteristics, the characteristics of the surrounding tissue and the operating frequency. In alternative embodiments, other suitable frequency ranges and penetration depths can be used.

After receiving the reflected ultrasound echoes, electric signals based on the reflected echoes are sent by transducers 40 over cables 33 through the catheter 28 to an image processor 42 (FIG. 1) in the console 34, which transforms them into 2-dimensional, typically sector-shaped ultrasound images. The image processor 42 typically computes or determines position and orientation information, displays real-time ultrasound images, performs 3-dimensional image or volume reconstructions and other functions, which will all be described in greater detail below.

In some embodiments, the image processor uses the ultrasound images and the positional information to produce a 3-dimensional model of a target structure of the patient's heart. The 3-dimensional model is presented to the physician as a 2-dimensional projection on a display 44.

In some embodiments, the distal end of the catheter also comprises at least one electrode 46 for performing diagnostic functions, therapeutic functions or both, such as electrophysiological mapping and radio frequency (RF) ablation. In one embodiment, the electrode 46 is used for sensing local electrical potentials. The electrical potentials measured by the electrode 46 may be used in mapping the local electrical activity on the endocardial surface. When the electrode 46 is brought into contact or proximity with a point on the inner surface of the heart 24 (FIG. 1), it measures the local electrical potential at that point. The measured potentials are converted into electrical signals and sent through the catheter to the image processor for display. In other embodiments, the local electrical potentials are obtained from another catheter comprising suitable electrodes and a position sensor, all connected to the console 34.

In alternative embodiments, the electrode 46 can be used to measure different parameters, such as various tissue characteristics, temperature, and blood flow. Although the electrode 46 is shown as being a single ring electrode, the catheter may comprise any number of electrodes in any form. For example, the catheter may comprise two or more ring electrodes, a plurality or array of point electrodes, a tip electrode, or any combination of these types of electrodes for performing the diagnostic and therapeutic functions outlined above.

The position sensor 32 is typically located within the distal end of the catheter 28, adjacent to the electrode 46 and the transducers 40. Typically, the mutual positional and orientational offsets between the position sensor 32, electrode 46 and transducers 40 of the ultrasonic sensor are constant. These offsets are typically used by the positioning processor 36 to derive the coordinates of the ultrasonic sensor and of the electrode 46, given the measured position of the position sensor 32. In another embodiment, the catheter 28 comprises two or more position sensors 32, each having constant positional and orientational offsets with respect to the electrode 46 and the transducers 40. In some embodiments, the offsets (or equivalent calibration parameters) are pre-calibrated and stored in the positioning processor 36. Alternatively, the offsets can be stored in a memory device (such as an electrically programmable read-only memory, or EPROM) fitted into the handle 29 of the catheter 28.

Position sensor 32 typically comprises three non-concentric coils (not shown), such as described in U.S. Pat. No. 6,690,963, cited above. Alternatively, any other suitable position sensor arrangement can be used, such as sensors comprising any number of concentric or non-concentric coils, Hall-effect sensors or magneto-resistive sensors.

Typically, both the ultrasound images and the position measurements are synchronized with the heart cycle, by gating signal and image capture relative to a body-surface electrocardiogram (ECG) signal or intra-cardiac electrocardiogram. In one embodiment, the ECG signal can be produced by the electrode 46. Since features of the heart change their shape 5 and position during the heart's periodic contraction and relaxation, the entire imaging process is typically performed at a particular timing with respect to this period. In some embodiments, additional measurements taken by the catheter, such as measurements of various tissue characteristics, temperature and blood flow, are also synchronized to the electrocardiogram (ECG) signal. These measurements are also associated with position measurements taken by the position sensor 32. The additional measurements are typically overlaid on the reconstructed 3-dimensional model, as will be explained below.

In some embodiments, the position measurements and the acquisition of the ultrasound images are synchronized to an internally generated signal produced by the system 20. For example, the synchronization mechanism can be used to avoid interference in the ultrasound images caused by a certain signal. In this example, the timing of image acquisition and position measurement is set to a particular offset with respect to the interfering signal, so that images are acquired without interference. The offset can be adjusted occasionally to maintain interference-free image acquisition. Alternatively, the measurement and acquisition can be synchronized to an externally supplied synchronization signal.

In one embodiment, the system 20 comprises an ultrasound driver (not shown) that drives the ultrasound transducers 40. One example of a suitable ultrasound driver, which can be used for this purpose is an AN2300™ ultrasound system produced by Analogic Corp. 25 (Peabody, Mass.). In this embodiment, the ultrasound driver performs some of the functions of the image processor 42, driving the ultrasonic sensor and producing the 2-dimensional ultrasound images. The ultrasound driver may support different imaging modes such as B-mode, M-mode, CW Doppler and color flow Doppler, as are known in the art.

Typically, the positioning and image processors are implemented using a general-purpose computer, which is programmed in software to carry out the functions described herein. The software may be downloaded to the computer in electronic form, over a network, for example, or it may alternatively be supplied to the computer on tangible media, such as CD-ROM. The positioning processor and image processor may be implemented using separate computers or using a single computer, or may be integrated with other computing functions of the system 20. Additionally or alternatively, at least some of the positioning and image processing functions may be performed using dedicated hardware.

Whether 3-dimensional anatomic images are reconstructed at the same time as the map is acquired or at different times, an image of the map of electrical potentials at the surface of the cavity is registered with the 3-dimensional image of the surface in a manner that is described hereinbelow.

2-Dimensional Anatomic Imaging

Figure 3:
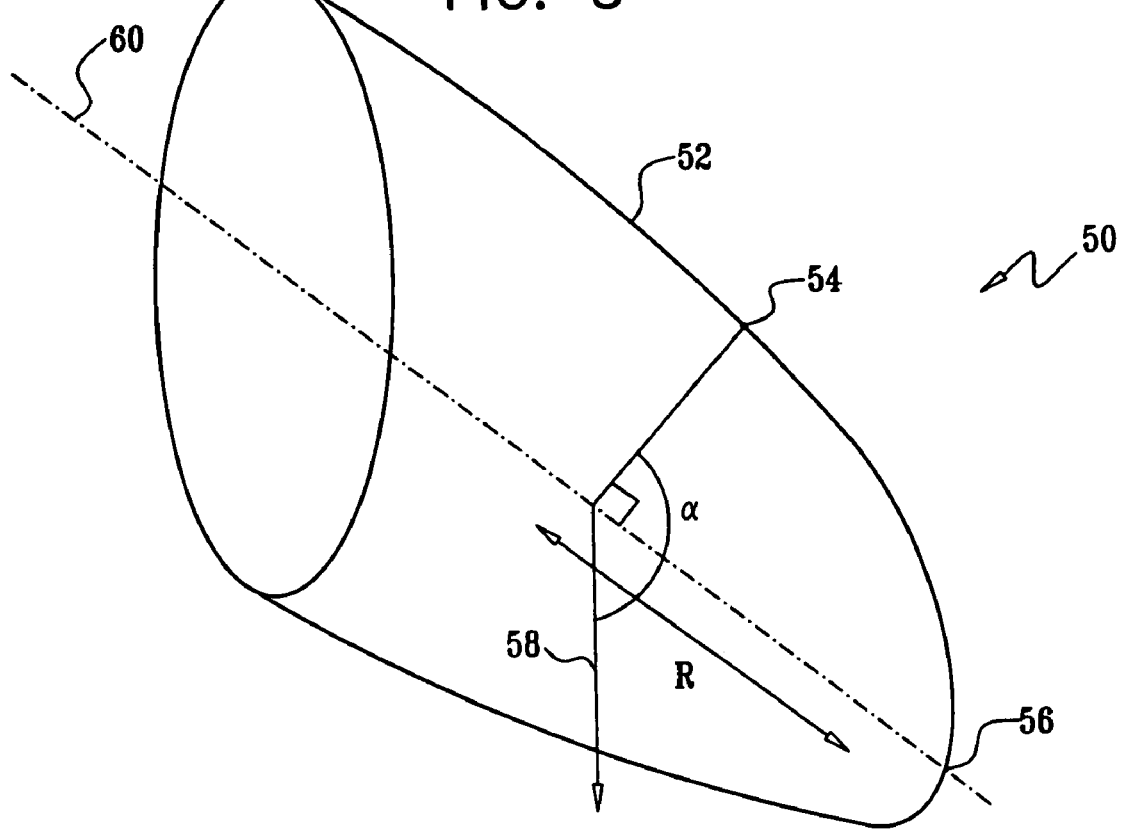
FIG. 3 is a simplified geometric representation of an electro-anatomical map, which has been prepared for registration with a diagnostic image in accordance with a disclosed embodiment of the invention.

Referring again to FIG. 1, gated images of the heart are created, e.g., ultrasound, SPECT, images and correlated with location data of the catheter 28, and registered with an electro-anatomical map, as described below. Suitable registration techniques are disclosed in U.S. Pat. No. 6,650,927, of common assignee herewith, and herein incorporated by reference. The technique is briefly described:

Reference is now made to FIG. 3, which is a simplified geometric representation of an electro-anatomical map 50, which has been prepared for registration with a diagnostic image in accordance with a disclosed embodiment of the invention. Details of the preparation of the map 50 are described in further detail hereinbelow. A surface 52 corresponds approximately to the endocardial surface of the heart. A coordinate system is defined, in which each point 54 on the surface 52 is represented by a distance R from an apex 56 and an angle α relative to a downward direction 58, i.e., ventrally and caudally relative to the subject 26 (FIG. 1). In order to register a diagnostic image with the map 50, an axis 60 and the apex 56 are identified on the map and aligned with corresponding features of the image to be registered, using location information provided by the sensors on the catheter 28 (FIG. 1). This is preferably automatic, but additionally or alternatively can be done or assisted by an operator. Other landmarks or fiducial marks on the heart can also be used in performing the alignment. The scale of the diagnostic image is adjusted so that its dimensions match that of the map 50 as closely as possible.

Figure 4:
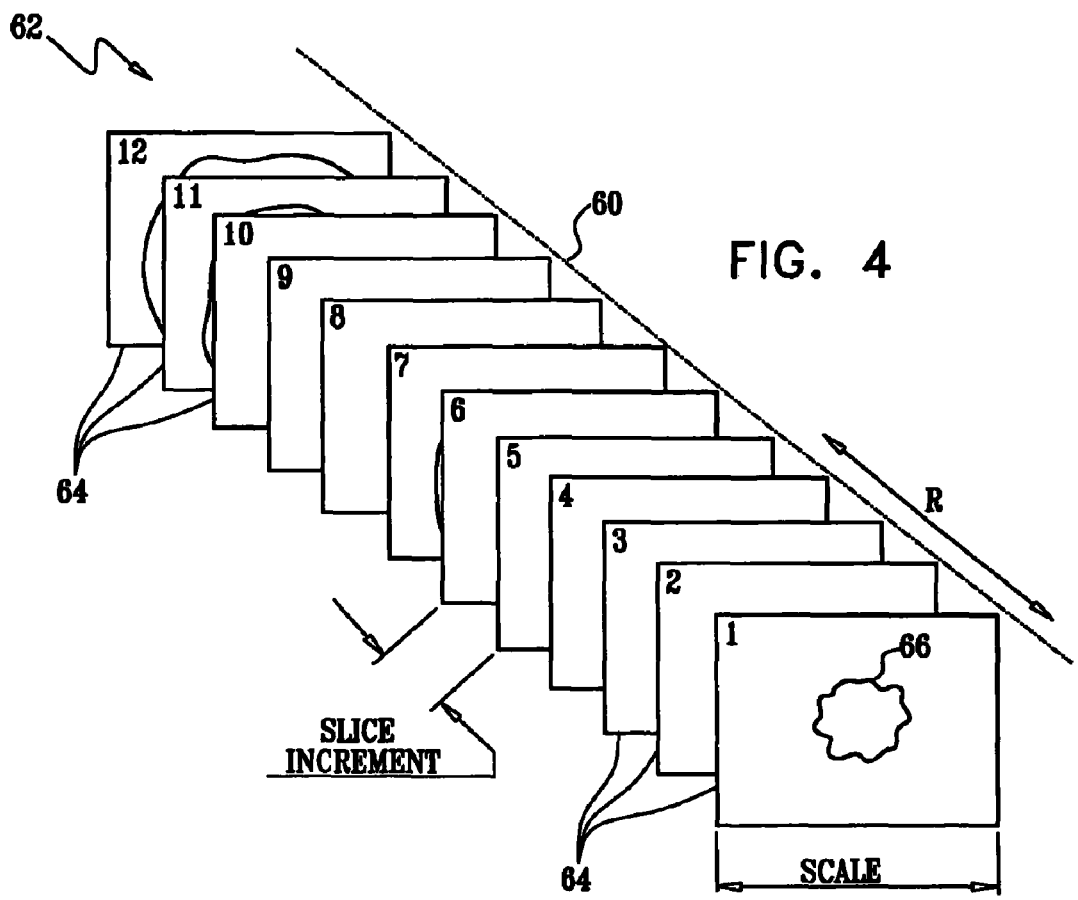
FIG. 4 is a schematic exploded view of a diagnostic image of a heart following registration with the map shown in FIG. 3, in accordance with a disclosed embodiment of the invention.

Reference is now made to FIG. 4, which is a schematic exploded view of a diagnostic image 62 of the heart 24 (FIG. 1) following registration with the map 50 (FIG. 3), in accordance with a disclosed embodiment of the invention. The view is generated using a bullseye rendition technique. The image 62 comprises a stack of parallel slices 64, which are perpendicular to the axis 60. The slices are typically taken at a fixed slice increment along the axis 60. Each slice shows a section 66.

It should be noted that 1-dimensional data can also be processed as above, simply by setting one of the two dimensions to a value of zero.

3-Dimensional Anatomic Imaging

Referring again to FIG. 1, 3-dimensional imaging is described in commonly assigned application Ser. No. 11/115, 002 filed on Apr. 26, 2005, entitled "Three-Dimensional Cardiac Imaging Using Ultrasound Contour Reconstruction", which is herein incorporated by reference. A brief description of the method will facilitate understanding of the present invention.

Essentially, the disclosed method combines multiple 2-dimensional ultrasound images, acquired at different positions of the catheter 28 as described above, into a single 3-dimensional model of the target structure. Typically, the physician inserts the catheter 28 through a suitable blood vessel into a chamber of the heart, and then scans the target structure by moving the catheter between different positions inside the chamber. In each catheter position, the image processor 42 acquires and produces a 2-dimensional ultrasound image.

Figure 5:
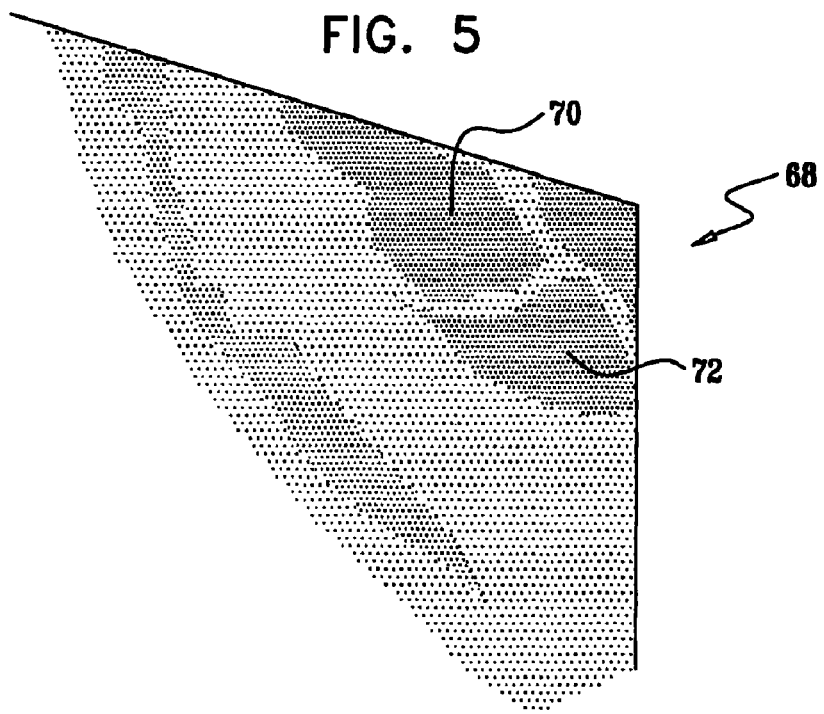
FIG. 5 shows an exemplary 2-dimensional ultrasound image acquired using the system shown in FIG. 1, in accordance with a disclosed embodiment of the invention.

Reference is now made to FIG. 5, which shows an exemplary 2-dimensional ultrasound image 68 acquired by the ultrasonic transducers of the catheter 28 (FIG. 1) at a particular position and generated by the image processor 42, in accordance with a disclosed embodiment of the invention. The image shows two distinct features 70, 72 of the heart.

Referring again to FIG. 1, the positioning subsystem of the system 20 measures and calculates the current position of the catheter 28. The calculated position is stored together with the corresponding ultrasound image 68 (FIG. 5). Typically, each position of the catheter 28 is represented in coordinate form, such as a six-dimensional coordinate (X, Y, Z axis positions and pitch, yaw and roll angular orientations).

In some embodiments, the catheter 28 performs additional measurements using the electrode 46. The measured parameters, such as local electrical potentials, are optionally overlaid and displayed as an additional layer on the reconstructed 3-dimensional model of the target structure.

The image processor 42 subsequently assigns 3-dimensional coordinates to the contours of interest, e.g., the features 70, 72 (FIG. 5), identified in the set of images. The location and orientation of the planes of these images in 3-dimensional space are known by virtue of the positional information, stored together with the images. Therefore, the image processor is able to determine the 3-dimensional coordinates of any pixel in the 2-dimensional images. When assigning the coordinates, the image processor typically uses stored calibration data comprising position and orientation offsets between the position sensor and the ultrasonic sensor, as described above.

Figure 6:
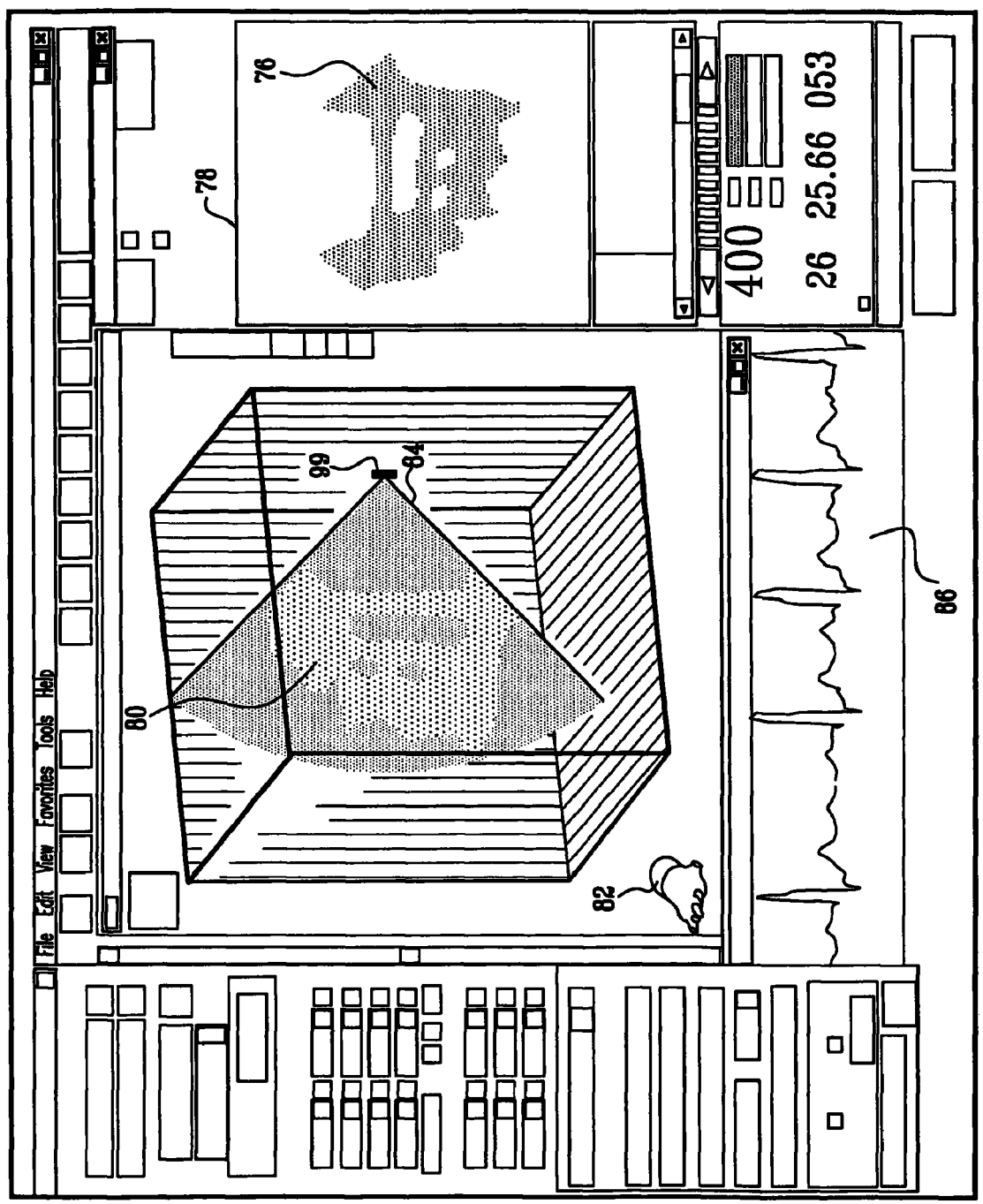
FIG. 6 is a 2-dimensional ultrasound image oriented and projected in 3-dimensional space, in accordance with a disclosed embodiment of the invention.

Reference is now made to FIG. 6, which is a display 74 of a 2-dimensional ultrasound image oriented and projected in 3-dimensional space in accordance with a disclosed embodiment of the invention. The display 74 is an exemplary split-screen display, as can be produced by image processor 42 (FIG. 1) and displayed on the display 44 of the system 20. A "raw" 2-dimensional version of an ultrasound image 76 is displayed in a separate window 78 on the right hand side of the display 74, appropriately oriented in 3-dimensional space, in accordance with a disclosed embodiment of the invention.

An isometric display at the center of FIG. 6 shows a projected image 80, produced by orienting and projecting the plane of the ultrasound image 76 in 3-dimensional space, in accordance with the position measurement of the position sensor 32 (FIG. 1). An orientation icon 82, typically having the shape of the imaged anatomical structure (a heart in this example), is displayed with the same orientation as the projected image 80. The icon 82 assists the physician in understanding the 3-dimensional orientation of the projected image 80.

A beam icon 84 is used in association with the projected image 80 to mark the area scanned by the ultrasound beam. As such, the icon 84 is oriented and displayed in the same plane as the projected image 80. The icon 84 may comprise a web-like or fan-like linear depiction, preferably in color, such as red. Alternatively, the icon 84 may comprise a colored line marking the perimeter of the area scanned by the beam to produce the projected image 80, or any other suitable means for visualizing the position and orientation of the ultrasound beam. In the example of FIG. 6, the icon 84 comprises two straight lines indicating the angular sector defined by the ultrasound beam. In some embodiments, an additional icon marking the location and position of the distal end of the catheter 28 (FIG. 1) is also displayed.

The projected image 80 is typically displayed inside a cube that marks the boundaries of the working volume. The working volume is typically referenced to the coordinate system of field radiating coils 30 (FIG. 1) of the positioning sub-system. In one embodiment, each side of the cube (i.e., the characteristic dimension of the working volume) measures approximately 12 cm. Alternatively, any other suitable size and shape can be chosen for the working volume, typically depending upon the tissue penetration capability of the ultrasound beam.

A signal display 86 at the bottom of the figure shows the ECG signal, to which the measurements are synchronized, as explained above.

When the system 20 (FIG. 1) operates in real time, the position and orientation of the projected image 80 and of the icon 84 change with the movements of the catheter 28. In some embodiments, the physician can change the angle of observation, zoom in and out and otherwise manipulate the displayed images using the interactive display. The user interface features described herein are shown as an exemplary configuration. Any other suitable user interface can be used.

In some embodiments, the system 20 (FIG. 1) and the associated user interface can be used for 3-dimensional display and projection of 2-dimensional ultrasound images, without reconstructing a 3-dimensional model. For example, the physician can acquire a single 2-dimensional ultrasound image and tag contours-of-interest on this image. The system 20 can then orient and project the ultrasound image in 3-dimensional space, in a manner similar to the presentation of projected image 80 (FIG. 6). If desired, during a medical procedure the system can continuously track and display the 3-dimensional position of the catheter performing the procedure (which may be different from the catheter acquiring the projected image 80) with respect to the projected image 80 and any identified features of interest.

The image processor 42 (FIG. 1) produces a 3-dimensional skeleton model of the target structure. The image processor arranges the tagged contours from some or all of the 2-dimensional images in 3-dimensional space to form the skeleton model. In some embodiments, the image processor 42 uses a "wire-mesh" type process to generate surfaces over the skeleton model and produce a solid 3-dimensional shape of the target structure. The image processor 42 projects contours of interest on the generated 3-dimensional model. The model is typically presented to the physician on the display 44 (FIG. 1).

Figure 7:
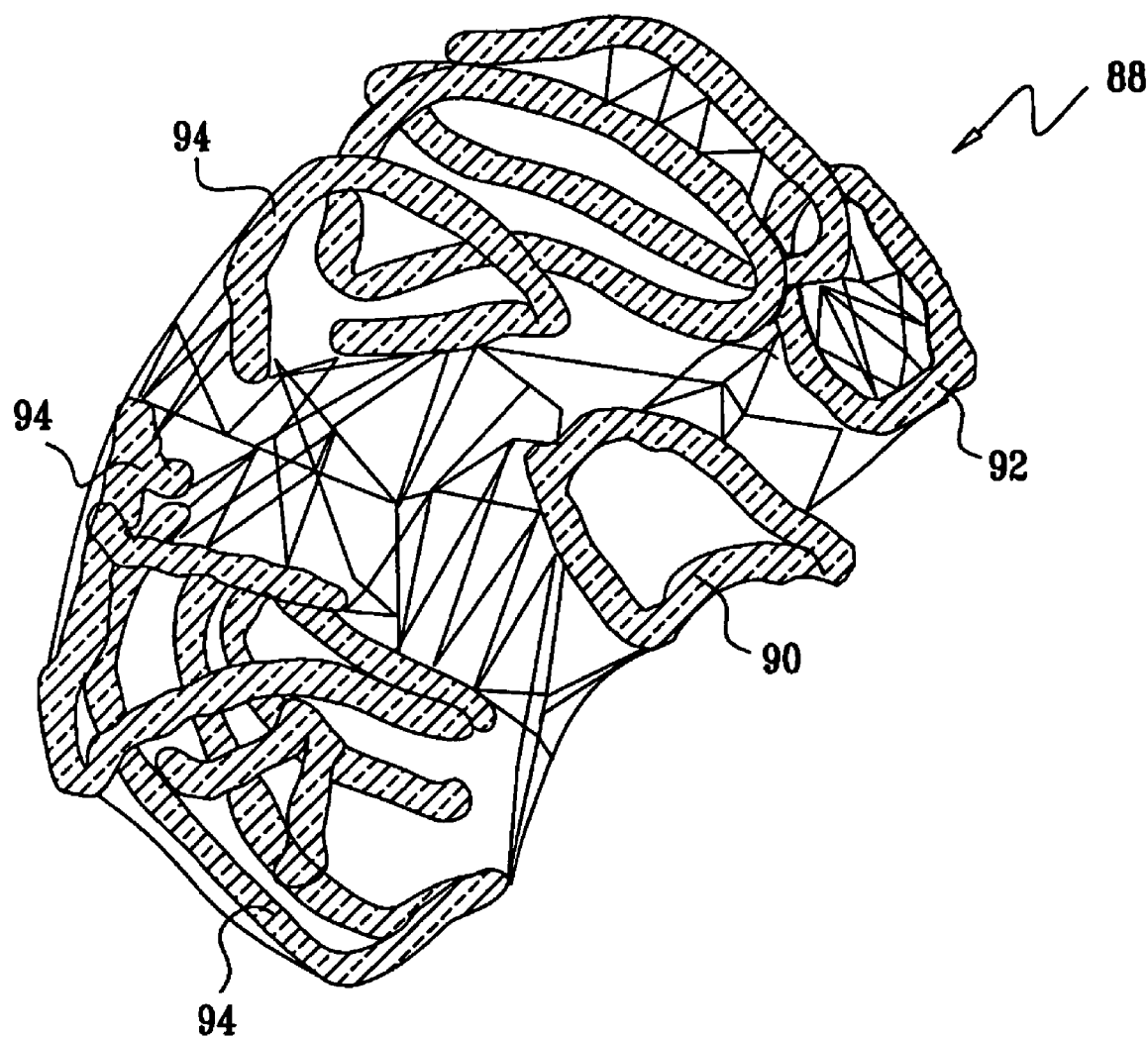
FIG. 7 is a skeleton model of a heart, in accordance with a disclosed embodiment of the invention.

Reference is now made to FIG. 7, which shows a skeleton model 88 of a target structure, in accordance with a disclosed embodiment of the invention. In FIG. 7, the target structure is the right ventricle of a heart, produced by the image processor 42 (FIG. 1) by 3-dimensional reconstruction as described above. Prior to generating the skeleton model 88, the image processor 42 automatically traces and reconstructs contours 90, 92 from untagged ultrasound images and also automatically reconstructs contours 94 from 2-dimensional physician-labeled counterparts (not shown).

3-Dimensional Electro-anatomical Maps

Referring again to FIG. 1, in some embodiments the system 20 supports a measurement of local electrical potentials on the surfaces of the target structure. In this measurement, each electrical activity data point acquired by the catheter 28 comprises an electrical potential or activation time value measured by the electrode 46 and the corresponding position coordinates of the catheter measured by the positioning sub-system. The image processor registers the electrical activity data points with the coordinate system of the 3-dimensional model and overlays them on the model. The electrical activity data points are typically measured when the electrode 46 is in contact with, or in close proximity to, the wall of the target structure. Therefore, the data points are typically superimposed on the 3-dimensional model of the structure.

Alternatively, a separate 3-dimensional electrical activity map (also referred to as an electro-anatomical map) can be generated and displayed. For example, a suitable electro-anatomical map can be produced by the above-referenced Carto-Biosense Navigation System. The electrical potential values may be presented using a color scale, for example, or any other suitable visualization method. In some embodiments, the image processor may interpolate or extrapolate the measured electrical potential values and display a full color map that describes the potential distribution across the walls of the target structure.

Image Registration

As noted above, it is desirable to register information imported from other imaging applications with an electro-anatomical map for display. According to the present invention registration of 2-dimensional or 3-dimensional images acquired by two different modalities is enabled by improved synchronization therebetween. The images from the two modalities may be concurrently acquired. Alternatively, one type of image may be pre-acquired and buffered, while the second type of image is acquired at or immediately prior to registration and display. An image grabber is used in an image processor and associated display unit to capture different images.

For example, concurrently or pre-acquired 2-dimensional or 3-dimensional ultrasound images may be registered and displayed together with an intra-operative electro-anatomical map.

Figure 8:
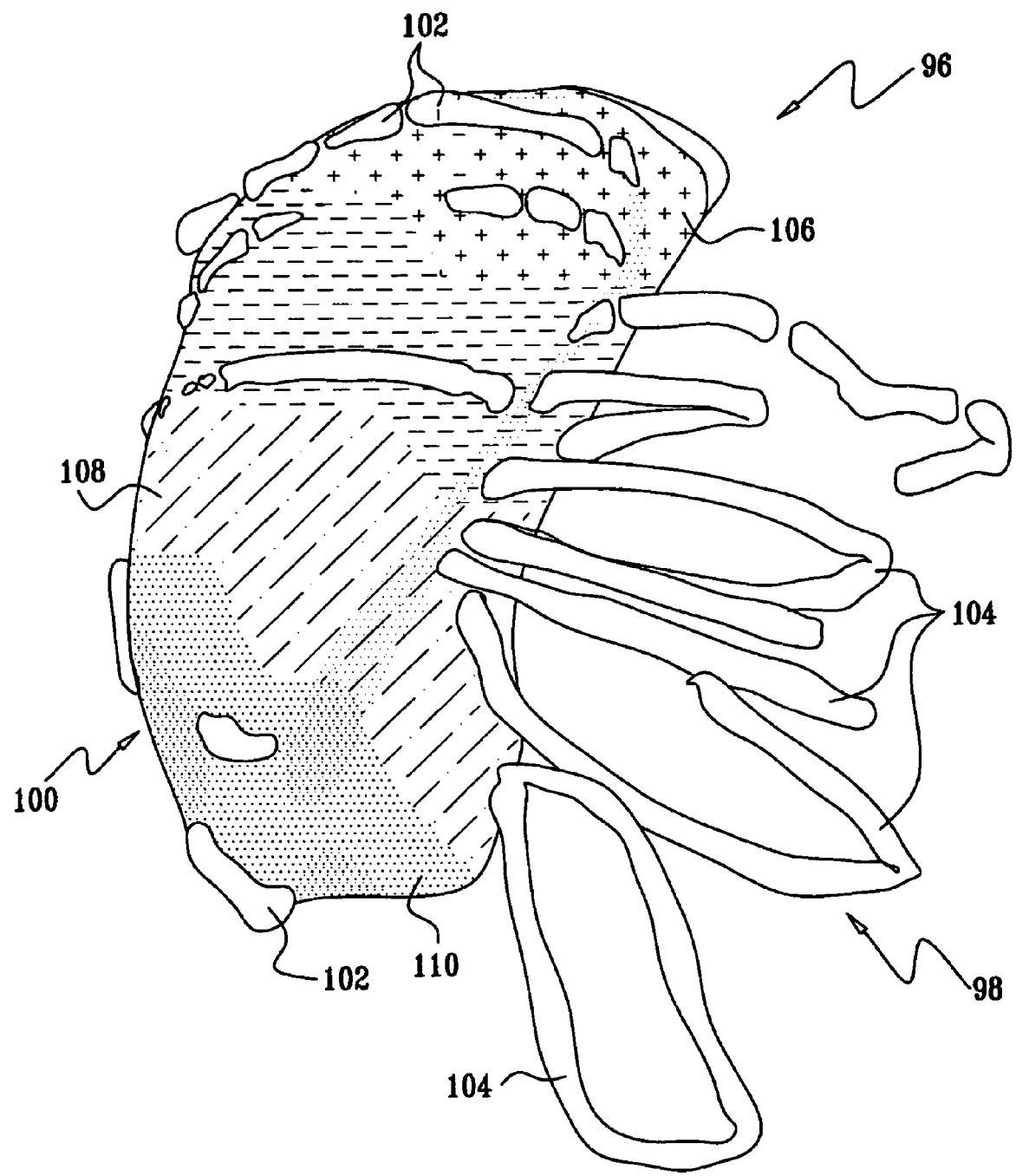
FIG. 8 is a composite image in which a skeleton model of a 3-dimensional ultrasound image of the heart is superimposed on a 3-dimensional electro-anatomical map of the right ventricle, in accordance with a disclosed embodiment of the invention.

Reference is now made to FIG. 8, which is an exemplary composite image 96 in which a skeleton model of a 3-dimensional ultrasound image 98 of the heart is superimposed on a 3-dimensional electro-anatomical map 100 of the right ventricle, in accordance with a disclosed embodiment of the invention. The skeleton model is similar to the skeleton model 88 (FIG. 7), having a plurality of contours 102, 104 outlining the right ventricle and left ventricle, respectively.

The electro-anatomical map 100 is a solid model, which corresponds to the surface of the right ventricle. Zones 106, 108, 110, shown in different shading patterns, represent different electrical potentials at a particular phase of the cardiac cycle.

Figure 9:
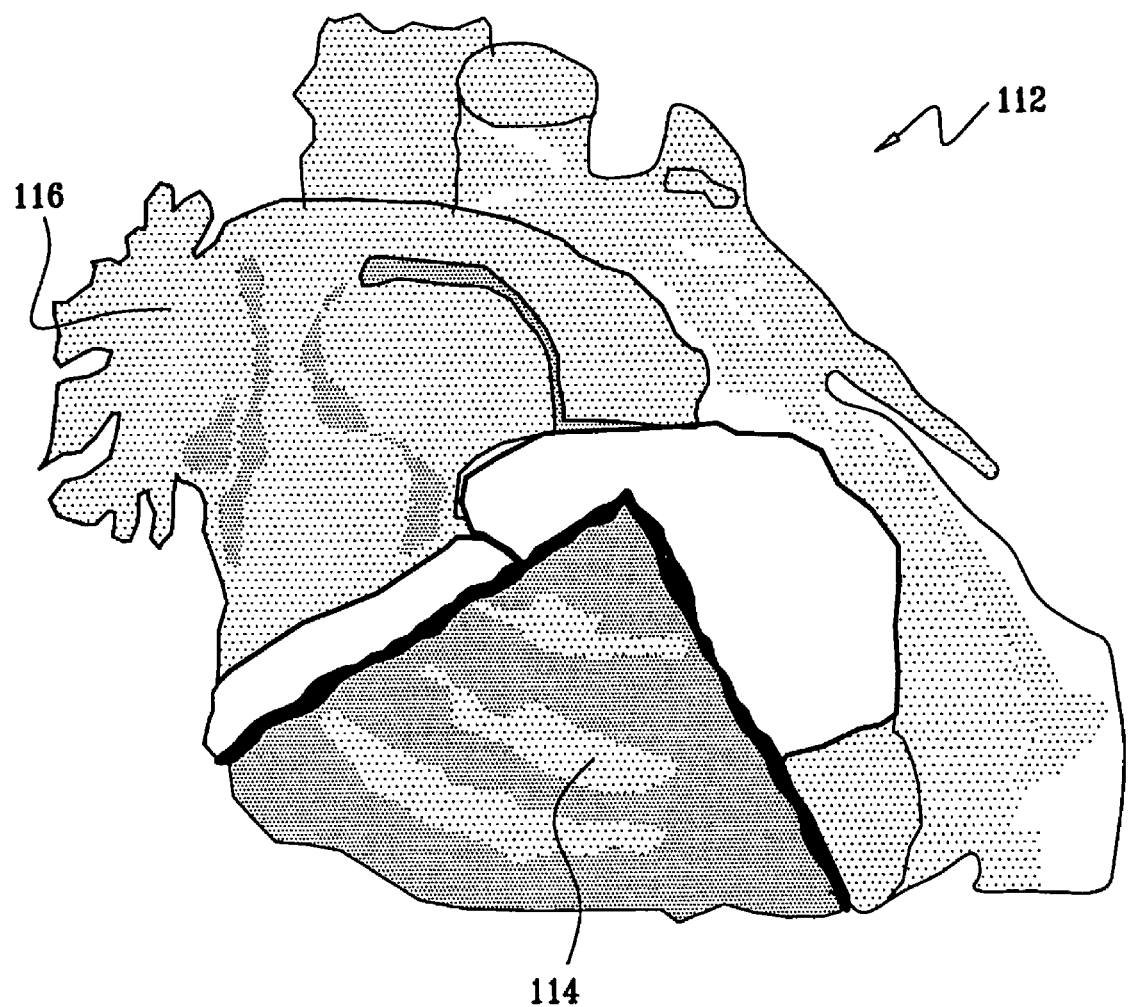
FIG. 9 is a composite image, in which a 2-dimensional ultrasound image is in registration with a pre-acquired 3-dimensional CT image, in accordance with a disclosed embodiment of the invention.

In other embodiments, pre-acquired computerized tomography, magnetic resonance imaging or x-ray information as anatomic images may be registered with a 2-dimensional image, or with a 3-dimensional ultrasound-based model and displayed together. Reference is now made to FIG. 9, which is a composite image 112, in which a presently acquired 2-dimensional ultrasound image 114 is registered with a pre-acquired 3-dimensional anatomic image 116 (in this example a CT image), in accordance with a disclosed embodiment of the invention. The composite image 112 can be displayed on the display 44 (FIG. 1) intraoperatively.

Additionally or alternatively, if additional parametric measurements were obtained during acquisition of the ultrasound image 114, such measurements can also be registered with the 3-dimensional model and displayed as an additional layer (often referred to as a "parametric map").

Referring again to FIG. 1, in some embodiments, the system 20 can be used as a realtime or near realtime imaging system. For example, the physician can reconstruct a 3-dimensional model of a target structure using the methods described above, as a preparatory step before beginning a medical procedure. The physician can tag any desired anatomical landmarks or features of interest, which are displayed on the 3-dimensional model. During the procedure, system 20 can continuously track and display the 3-dimensional position of the catheter with respect to the model and the tagged contours. The catheter used for performing the medical procedure may be the same catheter used for generating the 3-dimensional model, or a different catheter fitted with a suitable position sensor.

Synchronization

Referring again to FIG. 8, the ultrasound image 98 and the electro-anatomical map 100 can be acquired using different equipment, at different times, and even in different locations. When one or both of the images are being tracked in near-real time, and particularly when different equipment is used for the two modalities, propagation delays between the source equipment and the image processor 42 (FIG. 1) necessitate careful attention to synchronization of the two components of the composite image 96. Indeed, synchronization issues occur generally, in different embodiments of the system 20 (FIG. 1).

In one embodiment, wherein near real-time electro-anatomical data are acquired and superimposed upon previously acquired anatomic images or models, a constant predefined offset, which can be a temporal offset, is established between the electro-anatomical data and the anatomic image gating that compensates for system delays caused by image processing and image transfer from the source of the anatomic images to the image processor, which generates an electro-anatomical map from the electro-anatomical data.

Figure 10:
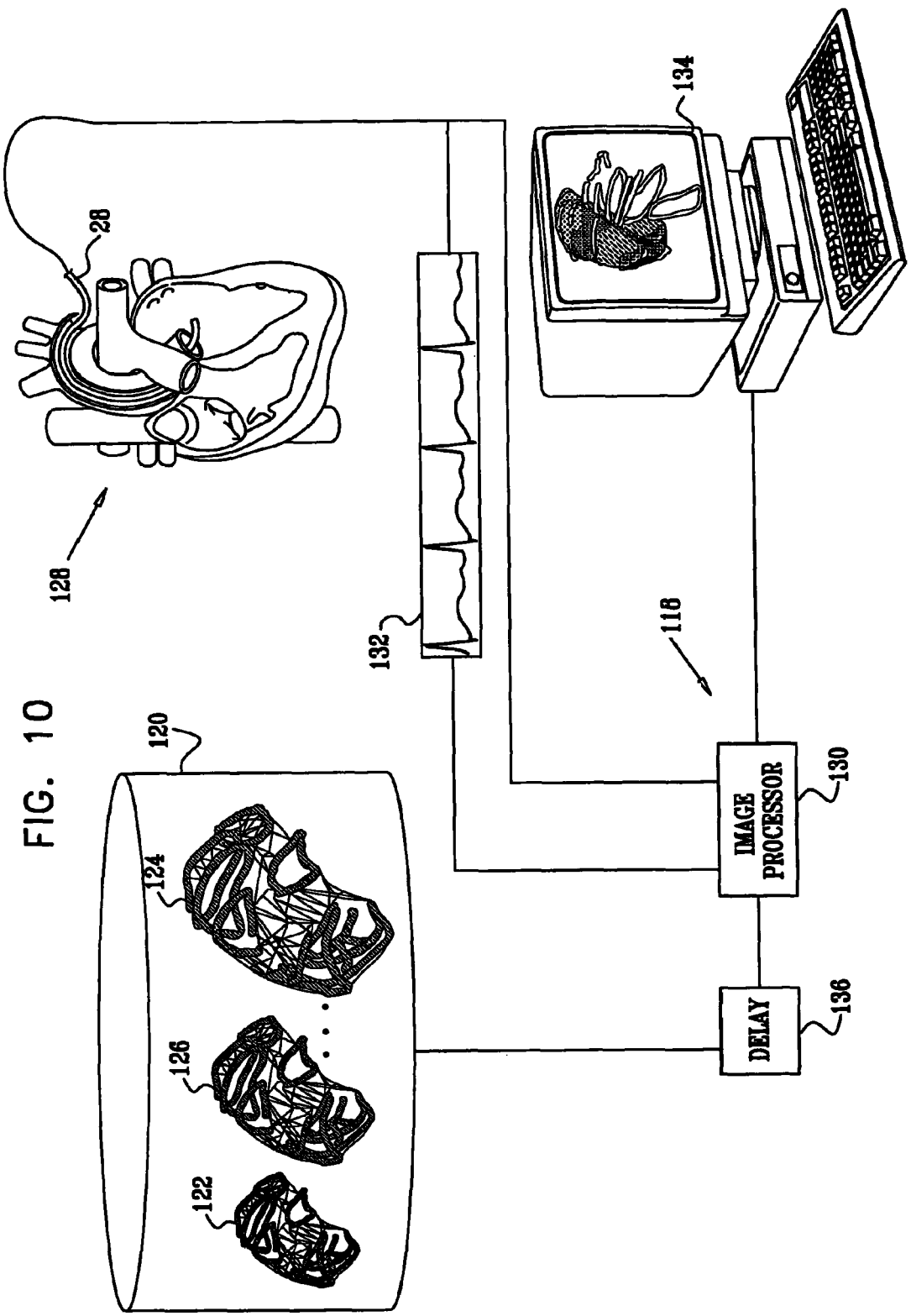
FIG. 10 is a schematic diagram of a system for synchronizing 3-dimensional ultrasound images with electro-anatomical mapping in near real time, in accordance with a disclosed embodiment of the invention.

Reference is now made to FIG. 10, which is a schematic diagram of a system 118, which is capable of synchronizing 3-dimensional ultrasound images with electro-anatomical mapping in near real time in accordance with a disclosed embodiment of the invention. A memory 120 has stored therein a series of pre-acquired 3-dimensional models, similar to the skeleton model 88 (FIG. 7) at different points in the cardiac cycle. Shown representatively are a systolic model 122, a diastolic model 124, and an intermediate model 126. In other embodiments of the system 118, the images stored in the memory 120 could be 2-dimensional ultrasound images, 2-dimensional tomographic images, or 3-dimensional images that were reconstructed at different points in the cardiac cycle, as described above.

An icon 128 represents a portion of the system 20 (FIG. 1), including the catheter 28 that is in a functional position for acquiring electrical activity data from a living subject, as described above, and in particular with reference to the electro-anatomical map 100 (FIG. 8). An image processor 130 accesses the memory 120, and also receives data from the sensors on the catheter 28. Synchronization data from the subject's ECG is available to the image processor 130 via an ECG signal 132. The image processor 130 constructs an electro-anatomical map at a point in the cardiac cycle, and registers the map with a corresponding one of the images stored in the memory 120. The result, similar to the composite image 96, is shown on a display 134. A delay 136 provides the necessary time adjustment to compensate for the time required by the image processor 130 to construct the electro-anatomical map. The delay 136 can be realized as a software module in the image processor 130, or may be implemented as a conventional electronic delay circuit.

Figure 11:
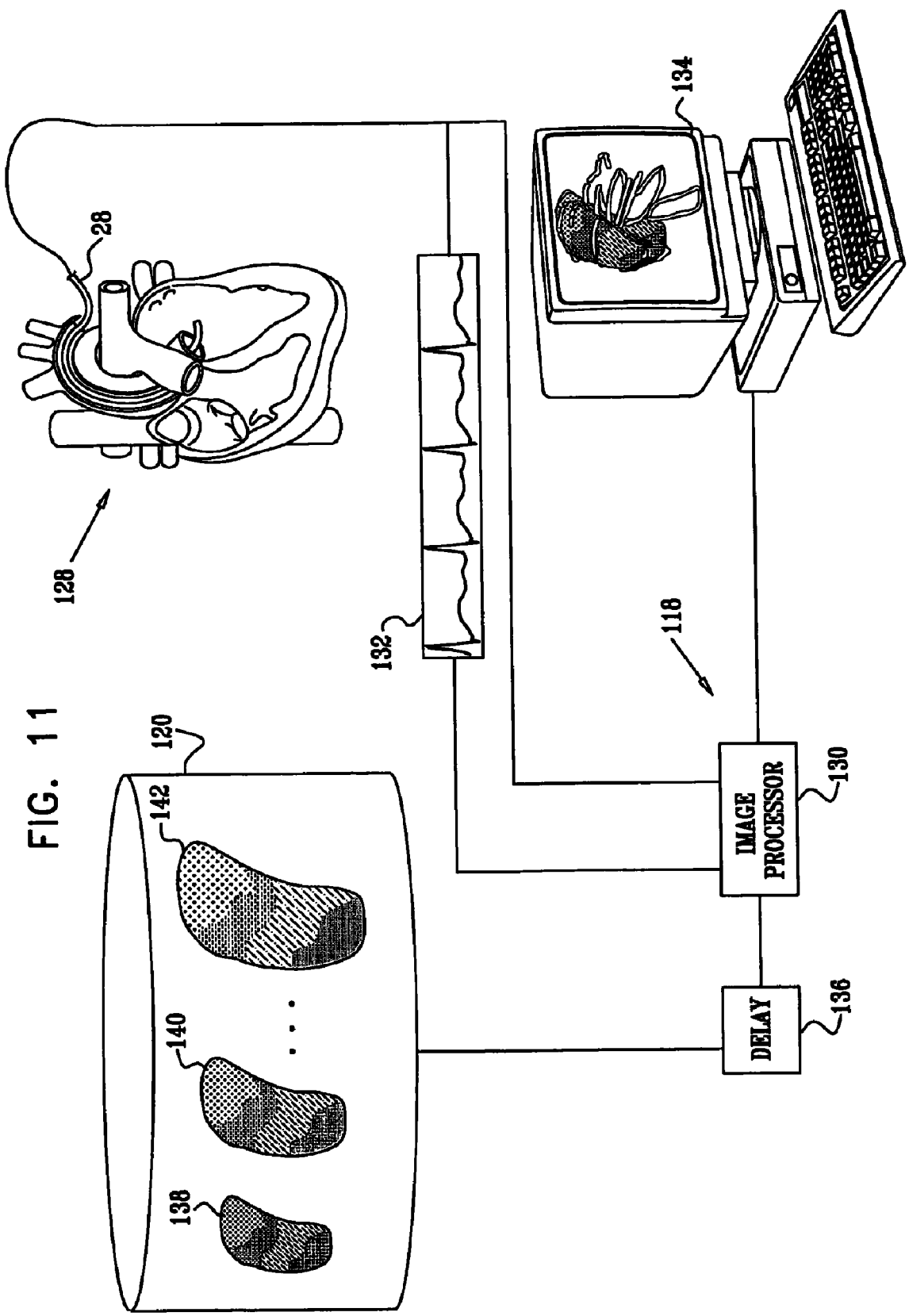
FIG. 11 is a schematic diagram of a system for synchronizing a previously acquired electro-anatomical map with a currently acquired series of 2-dimensional ultrasound images in near realtime, in accordance with an alternate embodiment of the invention.

Reference is now made to FIG. 11, which shows an alternative embodiment of the system 118, wherein a previously acquired electro-anatomical map is being registered with a currently acquired series of 2-dimensional ultrasound images in near realtime, in accordance with a disclosed embodiment of the invention. The memory 120 now stores a series of pre-acquired electro-anatomical maps that were constructed at different points in the cardiac cycle, including a systolic map 138, a diastolic map 140, and an intermediate map 142. A series of 2-dimensional ultrasound images is being acquired from the subject in near real-time and transferred to the image processor 130. The delay 136 is now configured to allow for the image processor 130 to construct a 3-dimensional skeleton model at selected points in the cardiac cycle. The result on the display 134 is similar to the composite image shown in FIG. 10.

Figure 12:
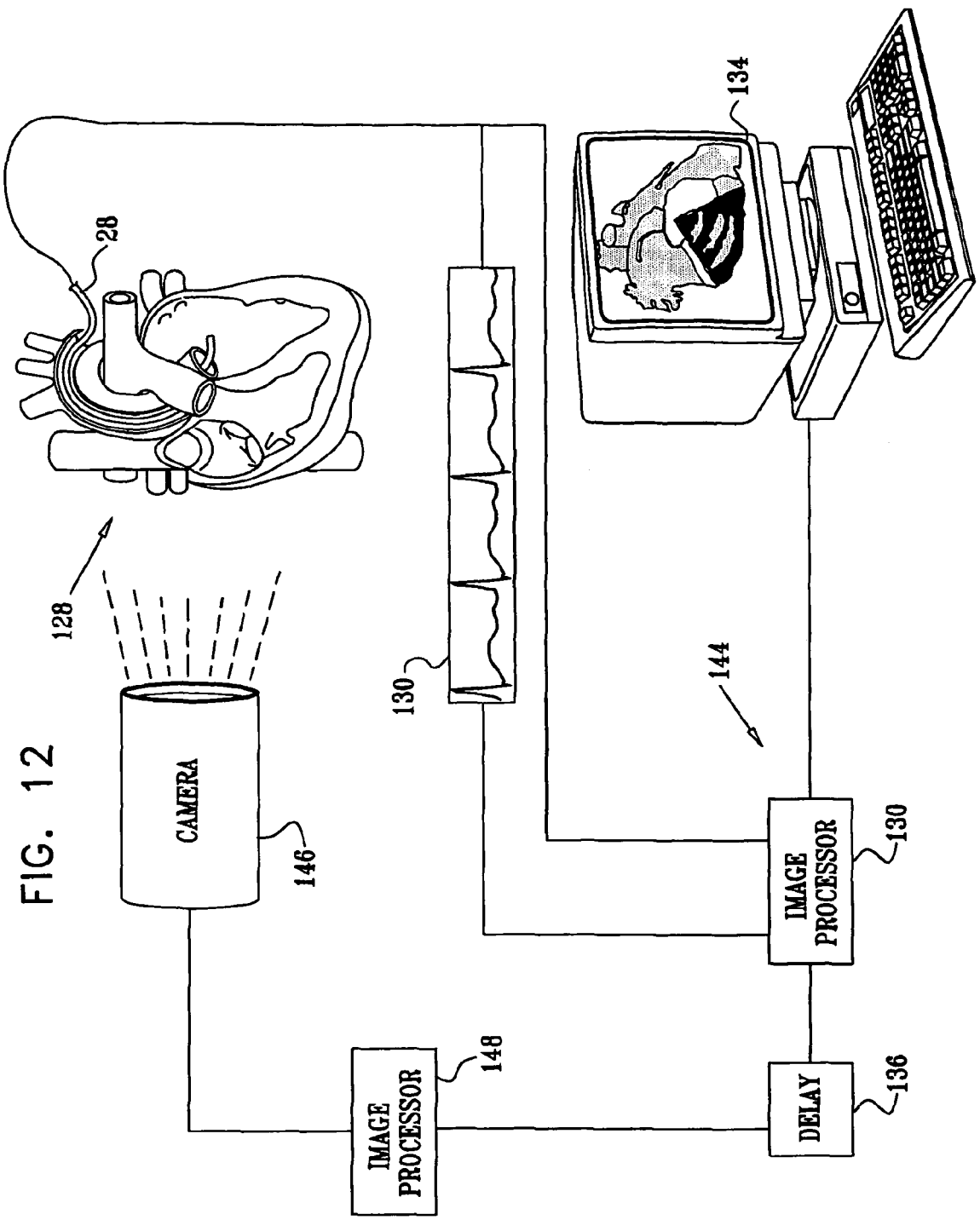
FIG. 12 is a schematic diagram of a system for synchronizing 3-dimensional electro-anatomical maps with concurrently acquired anatomic data in near realtime in accordance with an alternate embodiment of the invention.

Reference is now made to FIG. 12, which depicts a system 144, which is capable of synchronizing 3-dimensional electro-anatomical maps with concurrently acquired anatomic data in near realtime in accordance with an alternate embodiment of the invention. The memory 120 (FIG. 10) has been replaced by an image acquisition device, which in this example is a camera 146 suitable for acquiring PET images. The icon 128 represents a portion of the system 20 (FIG. 1), including the catheter 28 that is in operation to acquire electrical activity data, as described above with reference to FIG. 10. The system 144 is useful in correlating contractile and electrical myocardial function with the distribution of a suitably radiolabeled pharmaceutical in near realtime. A second image processor 148 constructs 3-dimensional anatomic images from the data acquired by the camera 146. The images produced by the image processor 148 are transferred to the image processor 130, with interposition of the delay 136 to adjust for time differences required for the image processors 130, 148 to perform their respective functions and for image transfer therebetween. The display 134 displays a composite image similar to the composite image 112 (FIG. 9).

Many other combinations of electro-anatomical maps and 3-dimensional anatomic images pre-acquired, or concurrently acquired will occur to those skilled in the art. In each case it is necessary to establish a value for the delay 136 in order to correctly register the two type of images.

EXAMPLE 1

A Carto XP system, available from Biosense-Webster, was used for producing an electro-anatomical map and for position calculations for the mapping catheter. A Sequoia™ system, available from Siemens Medical Solutions USA, Inc., Ultrasound Division Headquarters P.O. Box 7393 Mountain View, Calif. 94039-7393, was used for acquisition of ultrasound images, in conjunction with an AcuNav™ diagnostic ultrasound catheter, also available from Siemens. The AcuNav catheter was modified by the insertion of a location sensor adjacent to the ultrasound transducer. The location sensor was calibrated together with the ultrasound transducer, enabling the Carto XP system to calculate the position of every pixel in 2-dimensional ultrasound images. A video grabber card was added to the workstation of the Carto XP system. The video output from the Sequoia system was connected to the video grabber card. The ultrasound signals from the AcuNav catheter were connected to the Sequoia system, and the position signals from the location sensor were connected to the Carto XP system using separate cables.

The CARTO XP system was configured to receive the position information of the location sensor every 10 ms. The video image was generally captured by the video grabber card at 30 frames per second, although the video grabber card was capable of a framing rate of 60 frames per second. To facilitate the use of the position information together with cyclic 2-dimensional ultrasound images, it was necessary to correctly pair ultrasound images or frames with position data on the electro-anatomical map, at different points in the cardiac cycle, using an ECG-determined gating point as a reference.

In one approach, this was accomplished by inspecting a first buffer of time-stamped ultrasound utrasound images, and a second buffer of electro-anatomical map images showing location data in order to determine the image of the first buffer that was closest to a selected point in the cardiac cycle, using the gating point as a reference. The position of the catheter and the image used must be as close as possible to the annotation gating point. There are positions every 10 ms and the closest was selected and paired with the position information.

Alternatively, an image at a selected point of the cardiac cycle can be selected from the first buffer. The second buffer is then inspected in order to identify the electro-anatomical map image or the location data of the mapping catheter closest in time to the selected image from the first buffer.

EXAMPLE 2

Yet another method of establishing a delay is to measure the time interval between the time the position of the catheter was determined and the time at which corresponding image is presented. A time reference is established by generating interference in the ultrasound image using a pulsed RF signal in the imaging frequency (~7 MHz). The CARTO XP system was triggered at the moment that the interference was produced in order to obtain position data of the catheter. Than a delay in time is determined by the difference between the time at which the catheter position was sampled and the time stap of the image having the interference, as grabbed by the Carto XP system. This interval is then calculated and used as a constant delay.

Figure 13:
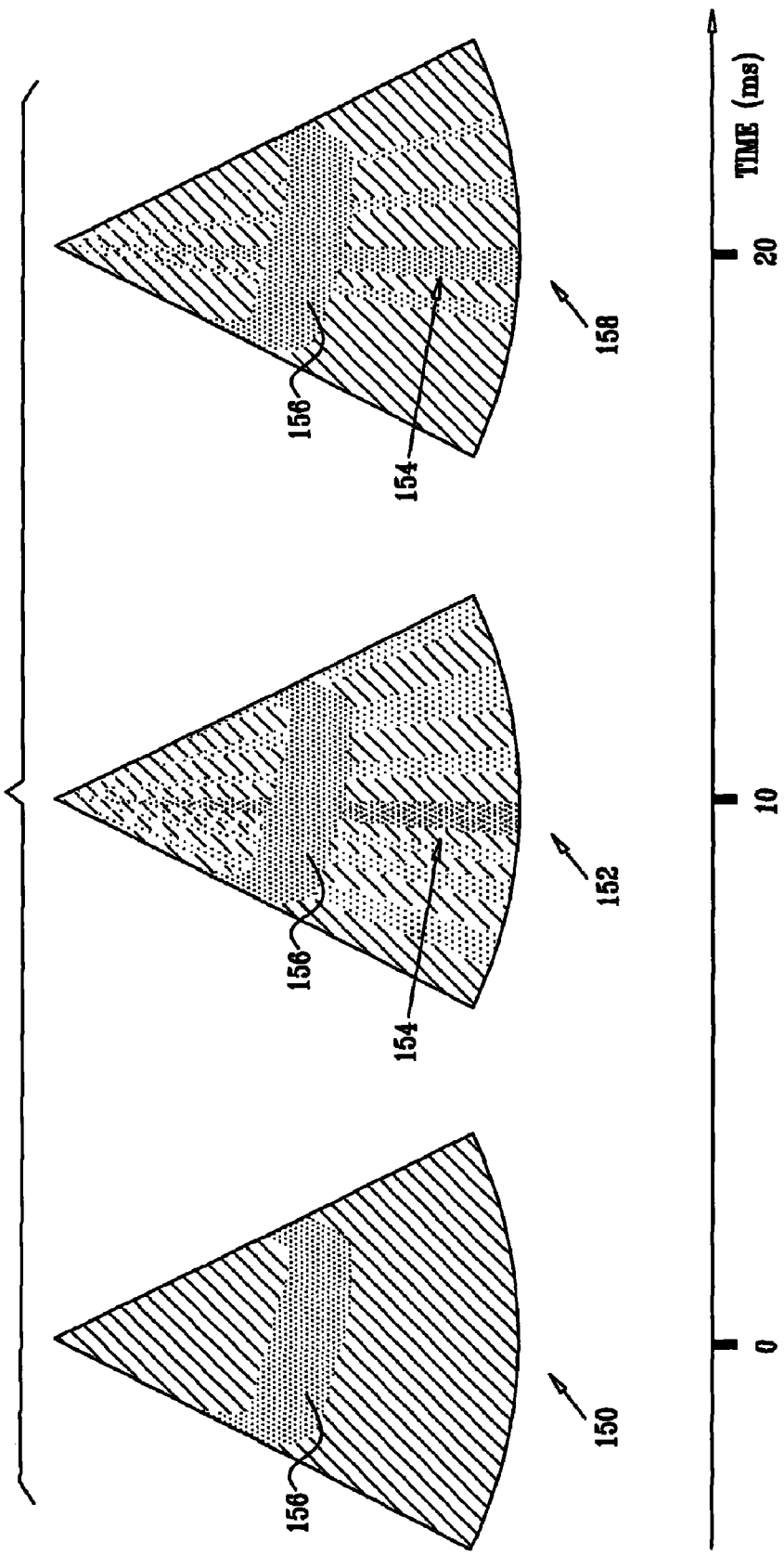
FIG. 13 is a series of three ultrasound images of the heart acquired at 10 ms 5 intervals in order to establish a delay offset in accordance with a disclosed embodiment of the invention.

Reference is now made to FIG. 13, which is a series of three ultrasound images of the heart acquired at 10 ms intervals in order to establish a delay offset in accordance with a disclosed embodiment of the invention. Data was acquired using the system of Example 1. Coordinates of both the catheter and points on the anatomic images are known, as explained above.

On the leftmost image 150, taken at time 20, there is no evidence of radiofrequency interference. In the center image 152, taken at time 10 ms, a burst of radiofrequency interference begins to be seen, as shown on the horizontal axis. This is manifested as a vertical streak 154. The inferior wall of the left ventricle is seen as a broad band 156.

The rightmost image 158 was acquired at time 20 ms. The streak 154 is considerably more prominent than on the image 152. On subsequent images (not shown) the streak 154 would fade and then disappear. Referring again to FIG. 10, in this system it is appropriate to set the value of the delay 136 such that the location data of the catheter lags the anatomic images by 20 ms.

Operation

Embodiment 1

Figure 14:
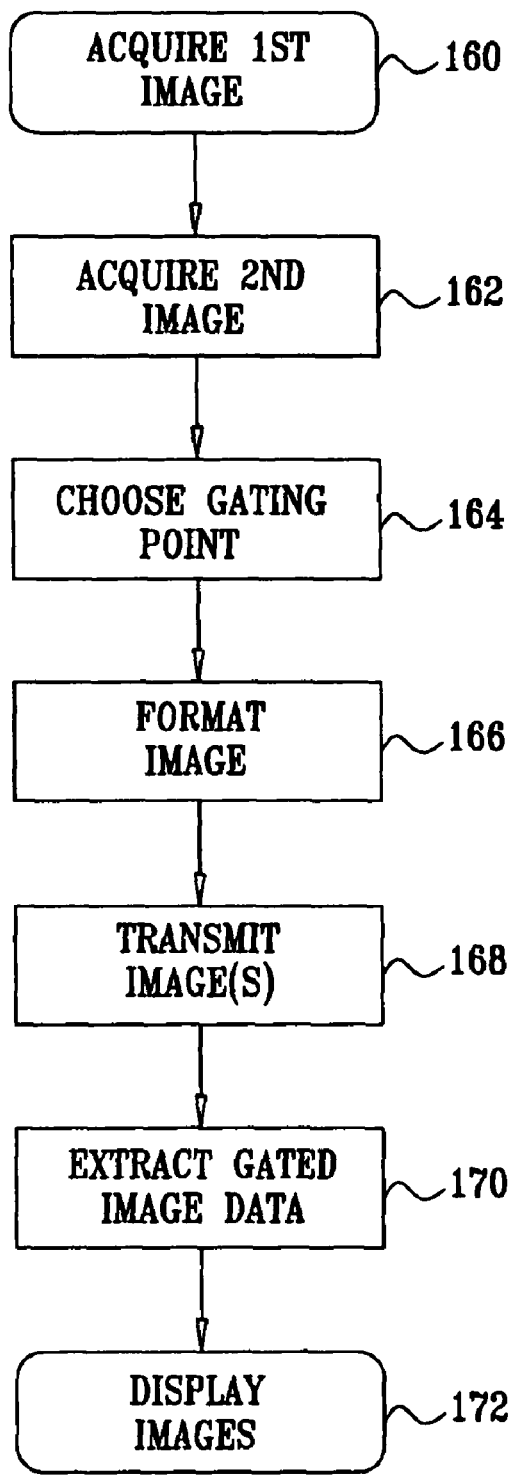
FIG. 14 is a flow chart illustrating a method of concurrently displaying two gated images that were acquired using different modalities, in accordance with a disclosed embodiment of the invention.

Reference is now made to FIG. 14, which is a flow chart illustrating a method of concurrently displaying two gated images acquired using different modalities, in accordance with a disclosed embodiment of the invention. The process steps are shown in a particular sequence in FIG. 14 for clarity of presentation. However, it will be evident that many of them can be performed in parallel, asynchronously, or in different orders.

At initial step 160 a first cyclical image is acquired by known techniques. This is a 3-dimensional electro-anatomical map, which can be obtained using the above-described Carto XP system.

Next, at step 162 a second cyclical image is acquired in near realtime. Typically this is a 3-dimensional ultrasound image of a structure having cyclical motion, such as the heart. However, the second image could be acquired by many other modalities, for example x-ray computed tomography or PET techniques.

Next, at step 164, a gating point is selected. This is normally done by a human operator. In the case of a cardiac study, the operator typically analyzes the electrical activity in the heart, typically in conjunction with a standard electrocardiogram, as well as taking into consideration the mechanical activity in the heart. For example, if a ventricular aneurysm were being evaluated in conjunction with electrical propagation, the gating point might be chosen differently than if no aneurysm were present. In general, points other than systole and diastole, the extrema of the motion cycle, are selected.

Next at step 166 at least one of the images is formatted and prepared for transmission to a display system. The gating point is included as synchronization information.

Next, at step 168, the formatted data is transmitted to the display system. Step 168 is performed in near realtime, during the acquisition of the anatomic image in step 162.

Next, at step 170, which is performed in near realtime, image data is extracted, limited to the data that corresponds to the chosen gating point. The same is done for the second image. The result is the equivalent images, which were acquired by gating at the time of acquisition. An advantage of step 170 is that the gating point need not be known in advance. Indeed, it is possible to display a plurality of images gated at different points in their motion cycle.

Next, at final step 172, both gated images are concurrently displayed at the same point in their motion cycle. The procedure terminates.

Embodiment 2

Figure 15:
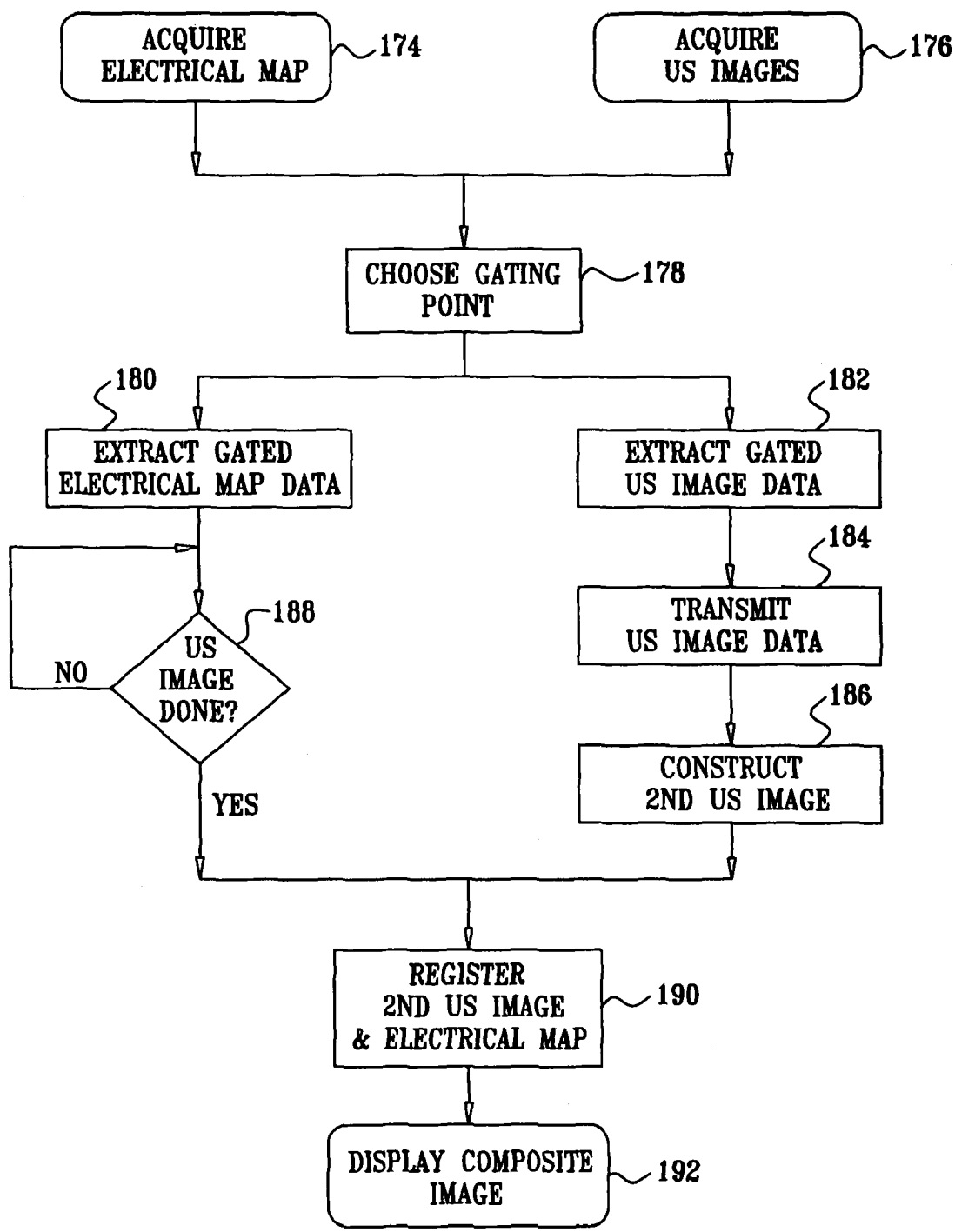
FIG. 15 is a flow chart illustrating a method of concurrently displaying two images concurrently acquired using different modalities, in accordance with an alternate embodiment of the invention.

Reference is now made to FIG. 15, which is a flow chart illustrating a method of concurrently displaying two gated images acquired using different modalities, in accordance with a disclosed embodiment of the invention. The steps described below can often conveniently be performed in different orders.

At step 174 a first cyclical image is acquired by known techniques. This is a 3-dimensional electro-anatomical map of the heart, which can be obtained using the above-noted Carto XP system.

Concurrently with step 174, at step 176 a 2-dimensional ultrasound image of the heart is acquired. This can be done using the same catheter as in step 174 However the second image could be acquired by other techniques, for example HIFU. Typically different equipment is used to process the ultrasound images and the electro-anatomical map.

Next, at step 178, a gating point is selected, as in step 164 (FIG. 14).

Next, at step 180 gated electrical data is extracted from the data acquired in step 174. This will be used to create an electro-anaiomical map at the selected gating point.

Concurrently with step 180, at step 182 gated image data is extracted from the ultrasound image data that was acquired in step 176.

For purposes of the following steps, it is assumed that an image processor in the equipment used to acquire the electro-anatomical map registers the two types of images. Alternatively, image processing for both types of images could occur in the ultrasound acquisition system, in which case a transfer of the electro-anatomical data would be performed.

At step 184 image data that was acquired in step 176 is transferred to an image processor. Then, at step 186 a 2-dimensional ultrasound image is prepared from the data.

Concurrently with step 184 and step 186, control proceeds from step 180 to delay step 188, where completion of the image transfer and construction in step 184 and step 186 is awaited. This step synchronizes the registration of the two types of images by the image processor.

After delay step 188 has completed, control proceeds to step 190 where the ultrasound image and electro-anatomical map are placed in registration to create a composite image as described above.

Then, at final step 192, the composite image is displayed.

Embodiment 3

In this embodiment a series of preacquired ultrasound images (or other anatomical images) are stored in a buffer. Selected buffered images are registered in near realtime with a presently acquired electro-anatomical map.

Figure 16:
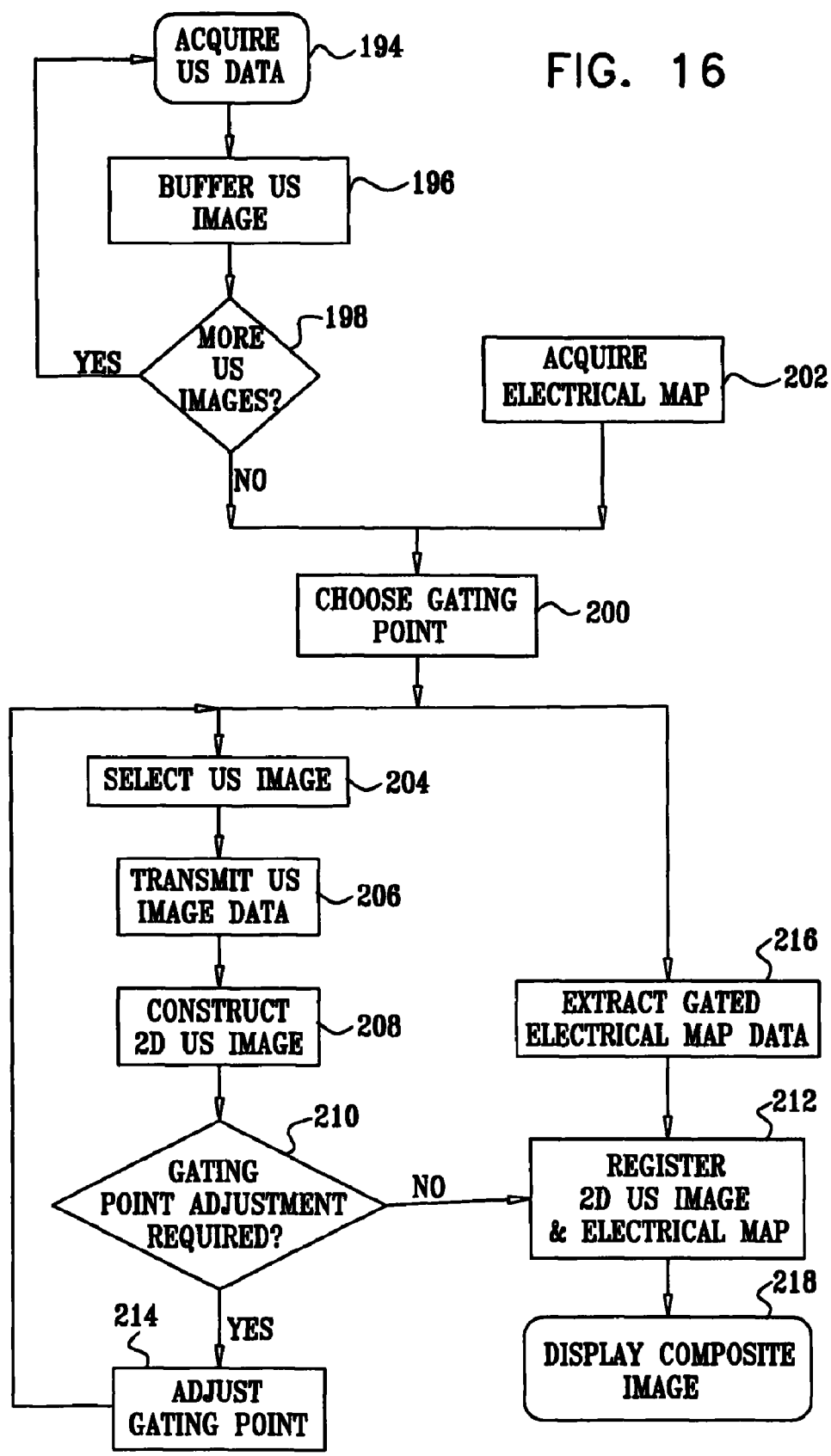
FIG. 16 is a flow chart illustrating a method of concurrently displaying two images acquired at different times using different modalities, in accordance with an alternate embodiment of the invention.

Reference is now made to FIG. 16, which is a flow chart illustrating a method of concurrently displaying two images acquired using different modalities, in accordance with an alternate embodiment of the invention. Some of the steps described below can often conveniently be performed in different orders.

At initial step 194 2-dimensional ultrasound data is acquired from the heart, as described above. This data is used to construct a member of a series of 2-dimensional images, each at a different phase of the cardiac cycle.

Next, at step 196, a 2-dimensional image is prepared from the data obtained in initial step 194, and stored in a buffer.

Control now proceeds to decision step 198, where it is determined if more 2-dimensional images remain to be prepared and stored. If the determination at decision step 198 is affirmative, then control returns to initial step 194.

If the determination at decision step 198 is negative, then control proceed to step 200, where a gating point is chosen.

At step 202 an electro-anatomical map is acquired, as described above. It is desired to register the electro-anatomical map with one or more of the 2-dimensional ultrasound images. Thus the steps that follow are generally performed repeatedly during an operative session with a subject. As the gating point varies, different members of the 2-dimensional ultrasound series are displayed in registration with different versions of the electro-anatomical map. Typically step 202 begins after all the 2-dimensional ultrasound images have been buffered, possibly in a different session, a different location, and using different equipment. Alternatively, only the raw image data is buffered, and the construction of 2-dimensional ultrasound images is deferred until the data is transferred to an image processor as described below. Step 196 and step 202 can be performed with different image acquisition units, which may be associated with different image processing units.

As in Embodiment 2, it is assumed that an image processor in the equipment used to acquire the electro-anatomical map registers the two types of images. Alternatively, image processing for both types of images could occur in the ultrasound acquisition system, in which case a transfer of the electro-anatomical data would be performed. The two sequences of steps described below with respect to the 2-dimensional ultrasound images and the electro-anatomical map are performed concurrently. The sequence pertaining to the 2-dimensional ultrasound images is described first.

Following completion of step 200, at step 204 one of the buffered 2-dimensional ultrasound images (or image data) is selected, at or near the chosen gating point.

Next, at step 206 the chosen image (or image data) is transferred to an image processor.

Next, at step 208, in embodiments where only image data is transferred, a 2-dimensional ultrasound image is constructed. If already constructed, then step 208 is omitted.

Control now proceeds to decision step 210, where it is determined if an adjustment to the gating point is necessary to provide a necessary delay to accommodate any image processing time or time required to transfer the image or data to the image processor. If the determination at decision step 210 is negative, then control proceeds to step 212, which is described below.

If the determination at decision step 210 is affirmative, then control proceeds to step 214, where any needed adjustment of the gating point of the 2-dimensional ultrasound images is performed to obtain synchronization between the gated 2-dimensional ultrasound image and the electro-anatomical map. The adjustment has the effect of retarding or advancing the image in the sequence that is registered with the electro-anatomical map. The adjustment can be accomplished by displaying the 2-dimensional ultrasound images in cine mode and manually retarding or advancing the phase of the loop as the case may be. Alternatively, the adjustment can be accomplished simply by selecting a different image from the sequence of 2-dimensional ultrasound images. Control returns to step 204.

Concurrently with the performance of steps 204, 206, 208, decision step 210, and step 214, a sequence of steps dealing with the electro-anatomical map is performed. At step 216, responsively to the gating point chosen in step 200, gated image data is extracted from the ultrasound image data that was acquired in step 202.

At step 212, which is performed upon exit from the loop at decision step 210 and following step 216, the selected 2-dimensional ultrasound image and gated electro-anatomical map are placed in registration to create a composite image as described above.

Then, at final step 218, the composite image is displayed.

In this and other embodiments disclosed above, a first set of data can be data of the structure being studied, and a second set of data can be positional data of a device being used to study the structure. Synchronized images prepared from both sets of data are then displayed in registration as described above.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for displaying images of a cyclically moving structure in a body of a living subject, comprising the steps of
selecting a gating point in a motion cycle of said structure;

acquiring data of said structure using a catheter having an imaging device and a position sensor;

acquiring position data comprising location and orientation coordinates of said imaging device of said catheter;

outputting said data of said structure and said position data to define an output of said data of said structure and an output of said position data, respectively;

synchronizing said output of said data of said structure with said output of said position data relative to said gating point to define synchronized data of said structure and synchronized position data, respectively, said step of synchronizing further comprising determining a time offset between said output of said data of said structure and said output of said position data relative to said gating point;

adjusting said time offset with respect to an interfering signal and acquiring images such that said images are acquired without interference;

repeating said step of synchronizing said output of said data of said structure with said output of said position data relative to said gating point; and concurrently displaying gated images derived from said synchronized data of said structure in registration with said synchronized position data at said gating point in said motion cycle.

2. The method according to claim 1, further comprising the step of transferring said synchronized data of said structure and said synchronized position data to a processing device.

3. The method according to claim 1, wherein said imaging device comprises an ultrasound transducer, and said position data comprises said location and orientation coordinates of said ultrasound transducer.

4. The method according to claim 3, wherein said catheter further comprises an electrode and said data of said structure comprise an electro-anatomical map.

5. The method according to claim 4, wherein said data of said structure is one-dimensional data.

6. The method according to claim 4, wherein said data of said structure is two-dimensional data.

7. The method according to claim 4, wherein said data of said structure is three-dimensional data.

8. The method according to claim 1, wherein said data of said structure comprises a plurality of frames acquired at different phases of said motion cycle and said step of synchronizing comprises associating said frames with a corresponding portion of said output of said position data.

9. The method according to claim 8, wherein said step of synchronizing further comprises the steps of:

generating an energy pulse while acquiring said data of said structure;

associating one of said frames with said energy pulse; and determining said time offset between said one frame associated with said energy pulse and said corresponding portion of said output of said position data.

10. The method according to claim 1, wherein said steps of acquiring data of said structure and acquiring position data are performed concurrently.

11. The method according to claim 1, wherein said steps of acquiring data of said structure and acquiring position data are performed non-concurrently.

12. The method of claim 1, further comprising:

generating an electro-anatomical map from a plurality of electro-anatomical data;

compensating for a system delay caused by image processing and image transfer of said plurality of electro-anatomical data to an image processor; and determining a constant time offset between said acquired data including said electro-anatomical data of said structure and said acquired position data and anatomic image gating, and said constant time offset being used as said time offset.

13. The method of claim 1, further comprising:

adjusting said gating point in said motion cycle of said structure for said acquired position data; and synchronizing an output of said acquired position data using said adjusted gating point with said output of said data of said structure.

14. A method for displaying images of a cyclically moving structure in a body of a living subject, comprising the steps of:

selecting a gating point in a motion cycle of said structure;

providing a catheter having an imaging device and a position sensor;

acquiring first data of said structure using said imaging device as a first modality;

acquiring second data as location and orientation coordinates of said structure using said position sensor as a second modality;

outputting said first data and said second data to define an output of said first data and an output of said second data, respectively;

synchronizing said output of said first data with said output of said second data relative to said gating point, said step of synchronizing further comprising determining a time offset between said output of said first data and said output of said second data relative to said gating point;

adjusting said time offset with respect to an interfering signal and acquiring images such that said images are acquired without interference;

repeating said step of synchronizing said output of said data of said structure with said output of said position data relative to said gating point; and concurrently displaying gated images derived from said synchronized output of said first data in registration with said synchronized output of said second data at said gating point in said motion cycle.

15. The method according to claim 14, further comprising the step of transferring said synchronized output of said first data and said synchronized output of said second data to a processing device.

16. The method according to claim 14, wherein said first modality comprises an ultrasound transducer, said first data comprise ultrasound signals and said second data comprise a location and orientation of said ultrasound transducer.

17. The method according to claim 14, wherein said first data comprise ultrasound signals and said second data comprise electrical activation map signals.

18. The method according to claim 17, wherein said first data is one-dimensional data.

19. The method according to claim 17, wherein said first data is two-dimensional data.

20. The method according to claim 17, wherein said first data is three-dimensional data.

21. The method according to claim 14, wherein said first data comprises a plurality of frames acquired at different phases of said motion cycle and said step of synchronizing comprises associating said frames with a corresponding portion of said output of said second data.

22. The method according to claim 21, wherein said step of synchronizing further comprises the steps of:

generating an energy pulse while acquiring said first data;

associating one of said frames with said energy pulse; and determining said time offset between said one frame associated with said energy pulse and said corresponding portion of said output of said second data.

23. The method according to claim 14, wherein said steps of acquiring first data and acquiring second data are performed concurrently.

24. The method according to claim 14, wherein said steps of acquiring first data and acquiring second data are performed non-concurrently.

25. A system for displaying images of a cyclically moving structure in a body of a living subject, comprising:
  electrical circuitry operative for selecting a gating point in a motion cycle of said structure;
  a catheter having a first acquisition device operative for acquiring first data of said structure using a first modality;
  a second acquisition device operative for acquiring second data as location and orientation coordinates of said structure using a second modality;
  a processor operative for synchronizing an output of said first acquisition device with an output of said second acquisition device relative to said gating point and for generating a first visual display from said output of said first acquisition device and a second visual display from said output of said second acquisition device, said synchronizing further comprising determining a time offset between said output of said first acquisition device and said output of said second acquisition device relative to said gating point, and wherein said time offset is adjusted with respect to an interfering signal and images are acquired without interference; and
  a display device linked to said processor for displaying said first visual display in registration with said second visual display at said gating point in said motion cycle.

26. The system according to claim 25, wherein said first data comprise ultrasound signals and said second data comprise electrical activation map signals.

27. The system according to claim 26, wherein said first data is one-dimensional data.

28. The system according to claim 26, wherein said first data is two-dimensional data.

29. The system according to claim 26, wherein said first data is three-dimensional data.

30. The system according to claim 25, wherein said first data comprises a plurality of frames acquired at different phases of said motion cycle and said processor is operative for synchronizing by associating a selected one of said frames with a corresponding portion of said output of said second acquisition device.

31. The system according to claim 30, further comprising an energy generator operative for generating an energy pulse while said first acquisition device is acquiring said first data, wherein said processor is operative for synchronizing by: associating said selected one of said frames with said energy pulse; and determining said time offset between said selected one of said frames associated with said energy pulse and said corresponding portion of said output of said second acquisition device.

* * * * *